(12) United States Patent
Kurohara et al.

(10) Patent No.: US 11,517,484 B2
(45) Date of Patent: Dec. 6, 2022

(54) ABSORBENT ARTICLE

(71) Applicant: DAIO PAPER CORPORATION, Ehime (JP)

(72) Inventors: Takeshi Kurohara, Ehime (JP); Yosuke Mori, Ehime (JP); Takashi Hagi, Ehime (JP)

(73) Assignee: DAIO PAPER CORPORATION, Ehime (JP)

( * ) Notice: Subject to any disclaimer, the term of this patent is extended or adjusted under 35 U.S.C. 154(b) by 869 days.

(21) Appl. No.: 15/511,371

(22) PCT Filed: Aug. 19, 2015

(86) PCT No.: PCT/JP2015/073221
§ 371 (c)(1),
(2) Date: Mar. 15, 2017

(87) PCT Pub. No.: WO2016/047319
PCT Pub. Date: Mar. 31, 2016

(65) Prior Publication Data
US 2017/0281430 A1   Oct. 5, 2017

(30) Foreign Application Priority Data

Sep. 26, 2014 (JP) .............................. JP2014-197465
Jun. 29, 2015 (JP) ................................ 2015-129709

(51) Int. Cl.
*A61F 13/84* (2006.01)
*A61F 13/551* (2006.01)
(Continued)

(52) U.S. Cl.
CPC ........ *A61F 13/8405* (2013.01); *A61F 13/496* (2013.01); *A61F 13/539* (2013.01);
(Continued)

(58) Field of Classification Search
CPC .. A61F 13/8405; A61F 13/496; A61F 13/539; A61F 13/5512; A61F 2013/53908;
(Continued)

(56) References Cited

U.S. PATENT DOCUMENTS 4,186,743 A    2/1980 Steiger
5,575,784 A *  11/1996 Ames-Ooten ....... A61F 13/5512
                                                 604/385.11
(Continued)

FOREIGN PATENT DOCUMENTS

EP        0348970 A2    1/1990
EP        0752239 A1    1/1997
(Continued)

*Primary Examiner* — Nicholas J. Weiss
*Assistant Examiner* — Gabriella E Burnette
(74) *Attorney, Agent, or Firm* — Andrus Intellectual Property Law, LLP

(57) ABSTRACT

The present invention is intended to provide an absorbent article that is excellent in anti-odor effect at the time of disposal. A pants-type disposable diaper includes an anti-odor tape that has a first gas barrier layer coupled to the pants-type disposable diaper and a second gas barrier layer that is stuck in a separable manner to either front or back surface of the first gas barrier layer via an adhesive agent containing an anti-odor agent. The anti-odor tape takes an anti-odor measure by separating the second gas barrier layer from the first gas barrier layer to expose the adhesive agent to the outside at the time of disposal of the pants-type disposable diaper.

6 Claims, 19 Drawing Sheets

(51) Int. Cl.
*A61F 13/496* (2006.01)
*A61F 13/539* (2006.01)

(52) U.S. Cl.
CPC ............. *A61F 13/5512* (2013.01); *A61F 2013/53908* (2013.01); *A61F 2013/8408* (2013.01)

(58) Field of Classification Search
CPC ............ A61F 2013/8408; A61F 13/472; A61F 13/535; A61F 13/49007; A61F 13/5515; A61L 15/46
See application file for complete search history.

(56) References Cited

U.S. PATENT DOCUMENTS

| | | | | |
|---|---|---|---|---|
| 5,769,833 | A * | 6/1998 | Hasse | A61F 13/8405 604/359 |
| 6,287,581 | B1 * | 9/2001 | Krzysik | A61L 15/24 424/402 |
| 6,926,704 | B2 * | 8/2005 | Andersson | A61F 13/5512 604/385.13 |
| 7,919,666 | B2 * | 4/2011 | Odorzynski | A61F 15/001 604/359 |
| 2004/0127866 | A1 | 7/2004 | Odorzynski | |
| 2005/0033214 | A1 | 2/2005 | Cantor | |
| 2008/0103470 | A1 | 5/2008 | Samuelsson et al. | |

FOREIGN PATENT DOCUMENTS

| | | | | |
|---|---|---|---|---|
| EP | 1214034 | A1 * | 6/2002 | ........... A61F 13/551 |
| EP | 1762207 | A1 | 3/2007 | |
| GB | 2353484 | A | 2/2001 | |
| JP | 7-250865 | | 10/1995 | |
| JP | 11-76302 | | 3/1999 | |
| JP | 11-509455 | A | 8/1999 | |
| JP | 2000-506426 | A | 5/2000 | |
| JP | 2000-506428 | | 5/2000 | |
| JP | 2000-350745 | A | 12/2000 | |
| JP | 2001-046423 | A | 2/2001 | |
| JP | 2001-340385 | A | 12/2001 | |
| JP | 2007-135661 | A | 6/2007 | |
| JP | 2008-541925 | A | 11/2008 | |
| JP | 2010-125127 | A | 6/2010 | |
| JP | 2010-154928 | A | 7/2010 | |
| JP | 2012-165857 | A | 9/2012 | |
| JP | 2012165857 | A * | 9/2012 | |
| JP | 2013-177424 | A | 9/2013 | |
| WO | WO 93/09818 | A1 | 5/1993 | |
| WO | WO 98/25562 | A1 | 6/1998 | |
| WO | WO 98/27843 | | 7/1998 | |

\* cited by examiner

ABSORBENT ARTICLE

TECHNICAL FIELD

The present invention relates to an absorbent article that includes an after-use anti-odor means excellent in the effect of anti-odor at the time of disposal.

BACKGROUND ART

Such absorbent articles as disposable diapers and sanitary napkins are, at the time of disposal after use, rolled or folded such that the used surfaces are inside (hereinafter, referred to as disposal state), and are temporarily stored in a highly air-tight storage container such as a sanitary bin or a diaper storage container, and when the amount of waste stored in the container reaches a certain degree, the waste was put into a garbage bag.

Accordingly, in general, the pants-type disposable diaper has an adhesive tape on the outer surface as a post-processing means for fixing the rolled diaper, and the tape-type disposable diaper has a fastener tape as a post-processing means for connecting the back side to the ventral side. The sanitary napkin is generally wrapped in an individual package sheet with an adhesive tape and fastened by the adhesive tape.

The absorbent article after use emits excretion odors, and even though it is stored in the air-tight container, it causes the user a feeling of discomfort when the container is opened and closed. To solve this problem, various anti-excretion odor means have been proposed.

Anti-odor measures are roughly divided into two kinds: masking by fragrances of perfumes; and odor adsorption by adsorption agents (odor-eliminating and deodorizing). There are examples of odor masking by which perfumes are released from micro capsules at the time of attachment and detachment of a fastener tape (refer to Patent Document 1), or perfumes are released with urination as a trigger (refer to Patent Document 2), or the like. In addition, there are examples of odor adsorption by adsorption agents: an odor-eliminating sheet containing zeolite is disposed inside the top sheet of an absorbent article (refer to Patent Document 3); the absorber of an absorbent article is wrapped in crepe paper containing an odor-eliminating agent (refer to Patent Document 4); and an absorbent article contains an odor-eliminating agent in the outer surface in the rolled state after use (refer to Patent Documents 5 and 6), and the like.

However, most of the conventional measures are structured to release perfumes or start odor adsorption immediately after manufacture, and therefore have the problems with durability and performance degradation that the anti-odor effect becomes weak at a point of time when the anti-odor measure is necessary, and the problem that there is no much choice in perfumes and adsorption agents to assure durability.

Meanwhile, the ones in which perfumes are released from micro capsules at the time of attachment and detachment of the fastener tape and the ones in which fragrances are diffused with urination as a trigger are excellent in performance. However, these measures have the problem that, when the absorbent article is rolled and fixed at the time of its disposal, the source of the perfume is hidden inside and the release of the perfume is suppressed. In addition, when these measures are applied to disposable diapers for infants, they exert the masking effect during use and may make it difficult to recognize the time for replacement of the diaper by the odor of the excretion. Further, these measures involve their respective issues: the former ones are essential to have micro capsules and the latter ones have a limited choice of perfumes.

CITATION LIST

Patent Document

Patent Document 1: JP-A No. H11-509455
Patent Document 2: JP-A No. 2013-177424
Patent Document 3: JP-A No. 2001-046423
Patent Document 4: JP-A No. 2000-350745
Patent Document 5: JP-A No. 2010-154928
Patent Document 6: JP-A No. 2010-125127

SUMMARY OF INVENTION

Technical Problem

A major object of the present invention is to provide an absorbent article that is excellent in anti-odor effect at the time of disposal.

Solution to Problem

The present invention for solving the foregoing problems is as follows:

An absorbent article including an anti-odor tape that has a first gas barrier layer coupled to the absorbent article and a second gas barrier layer that is stuck in a separable manner to either front or back surface of the first gas barrier layer via an adhesive agent containing an anti-odor agent, wherein the anti-odor tape takes an anti-odor measure by separating the second gas barrier layer from the first gas barrier layer at the time of disposal of the absorbent article to expose the adhesive agent to the outside.
(Operation and Effect)

The anti-odor tape is structured such that the adhesive agent containing the anti-odor agent is sandwiched between the first gas barrier layer and the second gas barrier layer to seal the anti-odor agent in the first gas barrier layer, the second gas barrier layer, and the adhesive agent, and the anti-odor agent is caused to take effect by a user's separating operation. This structure makes performance degradation less prone to occur. Moreover, since the adhesive agent containing the anti-odor agent is exposed to the outside at the time of disposal of the absorbent article, the anti-odor agent does not remain hidden inside or the effect of anti-odor is not suppressed. Accordingly, the absorbent article is highly effective in anti-odor measure at the time of disposal. In addition, the anti-odor agent hardly takes effect during use of the absorbent article, and therefore there is no fear that it is difficult to recognize the time for replacement of the diaper by the odor of excretion.

The absorbent article described herein, further including a fixing means that fixes the second gas barrier layer separated from the first gas barrier layer to the outer surface of the absorbent article.
(Operation and Effect)

By allowing the second gas barrier layer separated from the first gas barrier layer to be fixed to the outer surface of the absorbent article, it is possible to prevent the situation in which the second gas barrier layer is stuck again to the first gas barrier layer. In addition, in a mode in which, after the separation, the adhesive agent containing the anti-odor agent is left on both the first gas barrier layer and the second gas barrier layer, the exposed area of the adhesive agent can be doubled.

The absorbent article described herein, wherein the anti-odor agent is not sealed in micro capsules but is mixed into the adhesive agent.
(Operation and Effect)

The adhesive agent containing the anti-odor agent of the present invention is not used as a fastener tape fixing means as described in Patent Document 1 (the adhesive agent as a fastener tape fixing means is bonded to the outer surface of the diaper at the time of disposal and is not exposed to the outside), thereby causing less reduction in adhesive force. In addition, the anti-odor agent is enclosed in the first gas barrier layer, the second gas barrier layer, and the adhesive agent and is less prone to cause performance degradation. Therefore, the absorbent article is preferably structured in a simple manner in which the anti-odor agent is not sealed in micro capsules but is mixed directly into the adhesive agent.

The absorbent article described herein, wherein, as adhesive agents for sticking the second gas barrier layer in a separable manner to the first gas barrier layer, the adhesive agent containing the anti-odor agent is applied in an elongated shape, and an adhesive agent not containing the anti-odor agent is extended along both the longitudinal side edges of the adhesive agent containing the anti-odor agent.
(Operation and Effect)

The anti-odor agent of the present invention is enclosed in the first gas barrier layer, the second gas barrier layer, and the adhesive agent, but the peripheral surface of the adhesive agent is exposed to the outside between the first gas barrier layer and the second gas barrier layer. Accordingly, performance degradation progresses in the anti-odor agent due to the exposed part, although it is a limited amount, even before the separation of the second gas barrier layer. Therefore, it is preferred to apply the adhesive agent containing the anti-odor agent in an elongated pattern and block the both sides of the adhesive agent in the direction orthogonal to the longitudinal side by an adhesive agent not containing the anti-odor agent.

The absorbent article described herein, wherein the anti-odor tape is a post-processing tape used to fix the absorbent article in the rolled state, the post-processing tape is structured in such a manner that a belt-like body with gas barrier properties is folded longitudinally plural times so that a plurality of layers is stacked to become a folding state and the adjacent layers are bonded to each other by an adhesive agent, and when the folded post-processing tape is unfolded, either front or back surface of the post-processing tape has the adhesive agent for fixing the rolled state and the other surface has the adhesive agent containing the anti-odor agent.
(Operation and Effect)

The anti-odor tape is preferably configured with the use of the post-processing tape as described above to allow the anti-odor measure to be automatically taken at the time of disposal. In addition, in this mode, the adhesive agent for post-processing fixation and the adhesive agent containing the anti-odor agent are separate ones. The adhesive agent for post-processing fixation does not contain the anti-odor agent so that it is possible to prevent reduction in fixing force (as a matter of course, the adhesive agent for post-processing fixation may contain the anti-odor agent).

The absorbent article described herein, wherein the anti-odor tape is dedicated for anti-odor measure.

(Operation and Effect)

The anti-odor tape is not used also as a post-processing tape but is dedicated for anti-odor measure, which makes it possible to design freely the exposed area of the adhesive agent and the shape and arrangement of the anti-odor tape, thereby achieving a more desired anti-odor measure.

The absorbent article described herein, wherein the anti-odor agent includes a perfume and at least some of components of the absorbent article other than the anti-odor tape also include the perfume.
(Operation and Effect)

When the anti-odor agent includes the perfume, the other components of the absorbent article also include the perfume so that it is possible to make the fragrance stronger in stages before and after the separation of the anti-odor tape.

Advantageous Effects of Invention

As described above, according to the present invention, it is possible to provide the advantages of enhancing the anti-odor effect at the time of disposal, and the like.

DESCRIPTION OF EMBODIMENTS

An embodiment of the present invention will be described below in detail with reference to the accompanying drawings.

FIGS. 1 to 8 illustrate an example of pants-type disposable diaper 100. The pants-type disposable diaper 100 is composed of an outer body 12 that constitutes the outer surface (back surface) of the product and an inner body 200 that is stuck to the inner surface of the outer body 12. Reference sign Y represents the entire length of the diaper in an unfolded state (from the edge of a waist opening WO of a front body part F to the edge of a waist opening WO of a back body part B), and reference sign X represents the entire width of the diaper in the unfolded state.

The inner body 200 is a part absorbing and retaining excretion such as urine, and the outer body 12 is a part for supporting the inner body 200 on the wearer's body. The dot patterns in the cross-sectional views represent an adhesive as a joining means for joining the constituent members. The hot-melt adhesive may be applied in a solid, bead, curtain, summit, or spiral pattern as the adhesive. Instead of or in addition to this, resilient and elastic members are fixed by applying the hot-melt adhesive to the outer peripheral surfaces of the resilient and elastic members with the use of a comb gun or a Sure-Wrap application means. The joining means for joining the constituent members may be a welding means such as heat sealing or ultrasonic sealing.

(Inner Body)

Figure 1:
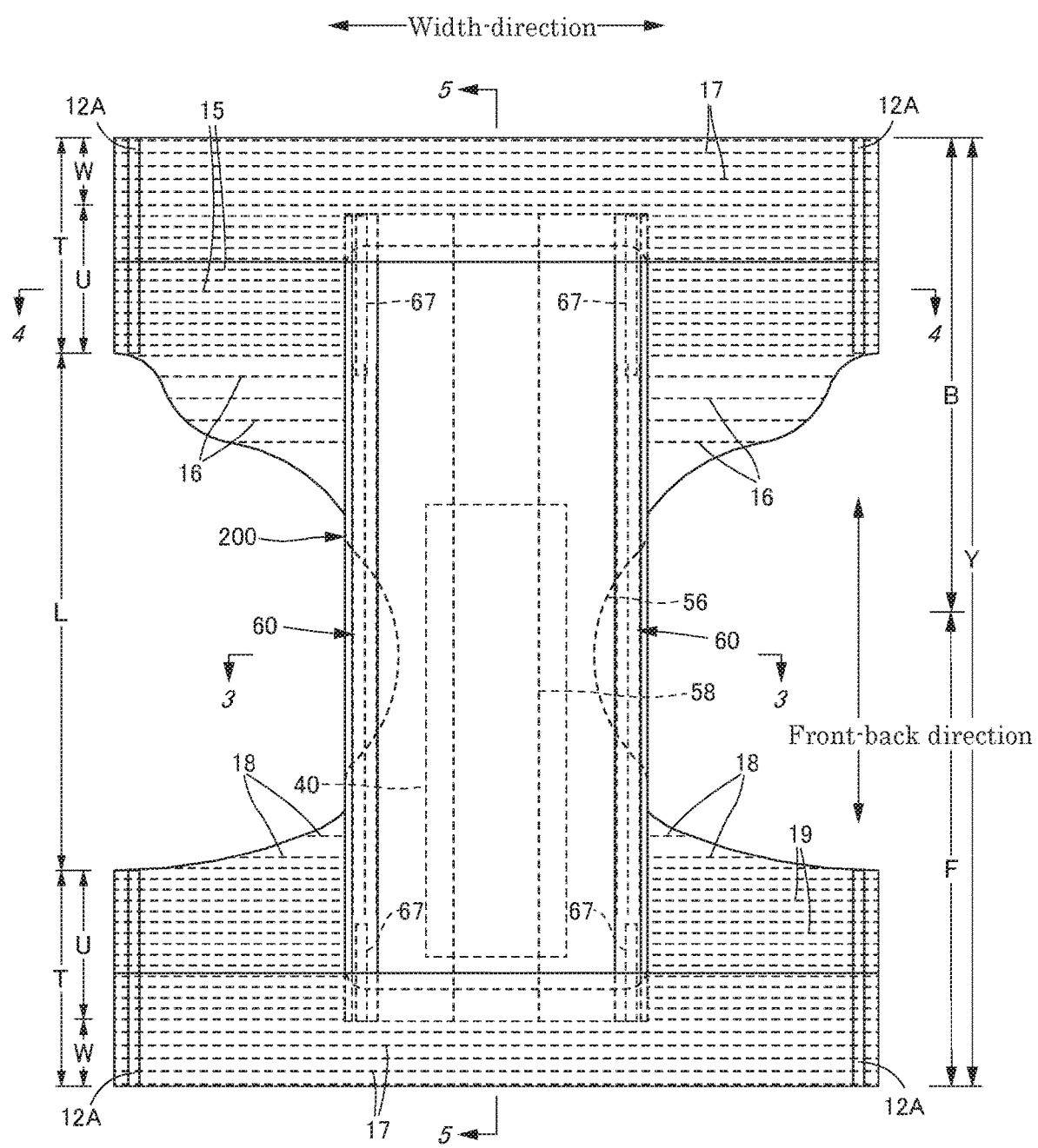
FIG. 1 is a plane view of an inner surface of a pants-type disposable diaper in an unfolded state.
Figure 2:
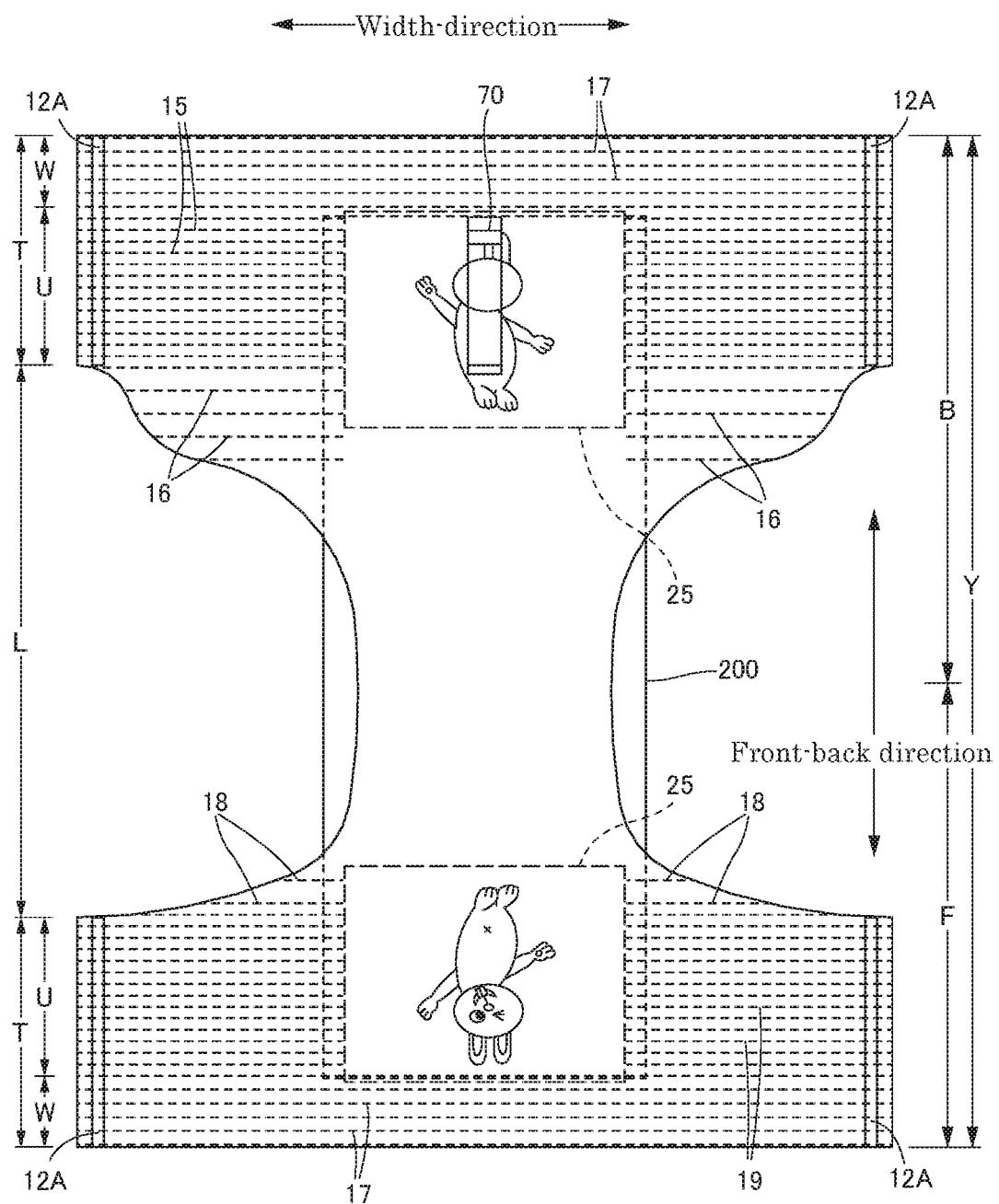
FIG. 2 is a plane view of an outer surface of the pants-type disposable diaper in the unfolded state.
Figure 3:
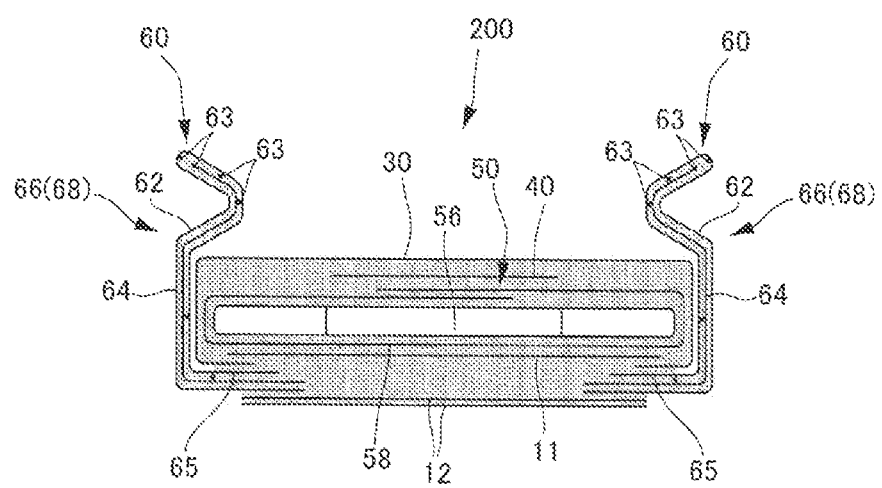
FIG. 3 is a cross-sectional view of FIG. 1 taken along line 3-3.
Figure 4:
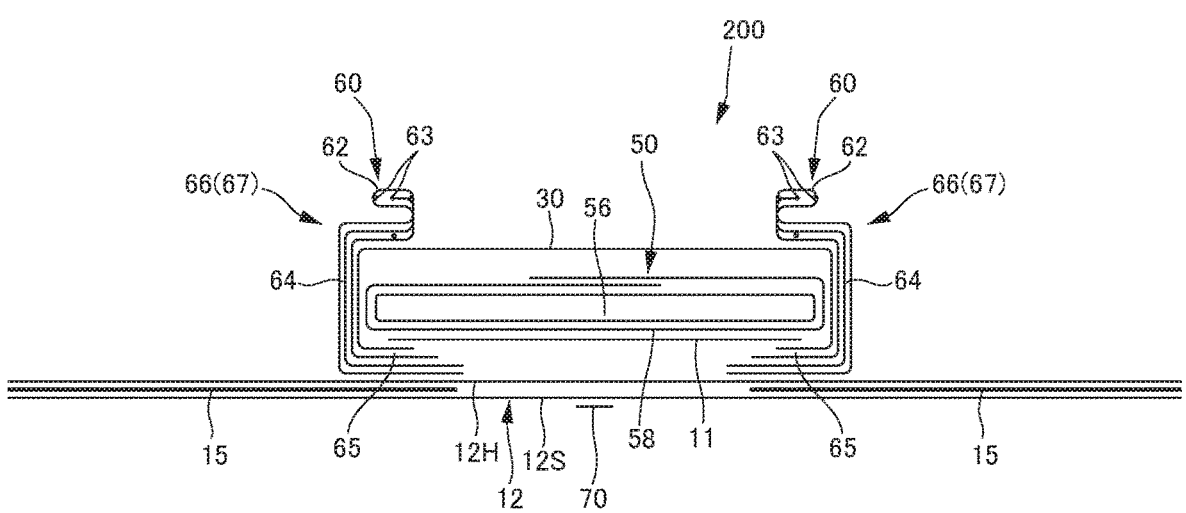
FIG. 4 is a cross-sectional view of FIG. 1 taken along line 4-4.
Figure 5:
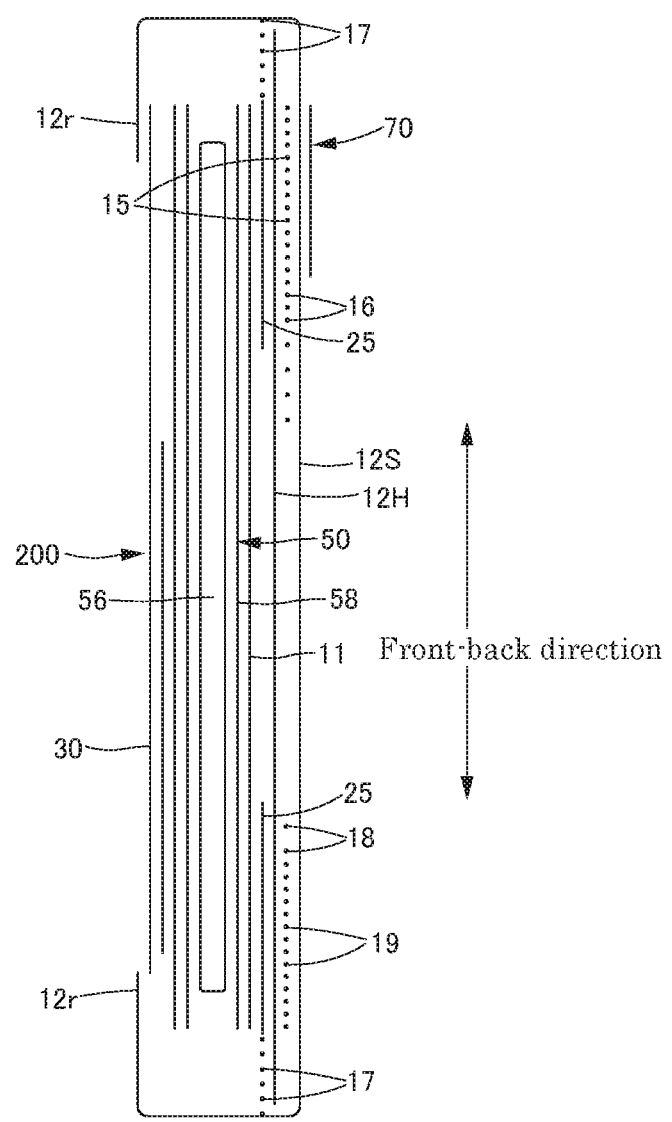
FIG. 5 is a cross-sectional view of FIG. 1 taken along line 5-5.

The inner body 200 is rectangular in the illustrated example but may have an arbitrary shape. As illustrated in FIGS. 3 to 5, the inner body 200 is a main body part that performs an absorption function and includes a top sheet 30 on the body side, a liquid impervious sheet 11, and an absorbent element 50 intervening between the top sheet 30 and the liquid impervious sheet 11. Reference sign 40 represents an interlayer sheet (second sheet) that is interposed between the top sheet 30 and the absorbent element 50 to move a liquid having passed through the top sheet 30 quickly to the absorbent element 50. Reference sign 60 represents three-dimensional gathers 60 that are provided on the both sides of the inner body 200 and stand toward the wearer's body to prevent excretion from leaking to the both sides of the inner body 200.

(Top Sheet)

The top sheet 30 is pervious to liquid and may be a porous or non-porous non-woven fabric sheet or a porous plastic sheet, for example. There is no particular limitation on raw fibers for the non-woven fabric. For example, the raw fibers may be synthetic fibers based on olefin such as polyethylene or polypropylene, polyester, or polyamide, reproduced fibers of rayon, cupra, or the like, natural fibers of cotton or the like, or mixed fibers or composite fibers of two or more of the foregoing fibers. The non-woven fabric may be produced by any processing method. The processing method may be any of publicly known methods such as spun-lacing, spun-bonding, thermal bonding, melt-blowing, needle punching, air-through processing, and point bonding, for example. For flexibility and drape properties, spun-bonding and spun-lacing methods are preferred. For bulkiness and softness, air-through processing, point-bonding, and thermal bonding methods are preferred.

The top sheet 30 may be composed of a single sheet or a layered sheet obtained by sticking two or more sheets each other. Similarly, the top sheet 30 may be composed of a single sheet or two or more sheets in a planar direction.

In the case of providing the three-dimensional gathers 60, it is preferred that the both sides of the top sheet 30 are extended up to the back side of the absorbent element 50 through the liquid impervious sheet 11 and the three-dimensional gathers 60, and are bonded to the liquid impervious sheet 11 and the three-dimensional gathers 60 by a hot-melt adhesive or the like to prevent liquid penetration.

(Interlayer Sheet)

To move the liquid having passed through the top sheet 30 quickly to the absorber, the interlayer sheet (called also "second sheet") 40 higher in liquid permission speed than the top sheet 30 may be provided. The interlayer sheet 40 can move the liquid quickly to the absorber with enhancement in absorption performance of the absorber and also can prevent a "reflowing" phenomenon of the absorbed liquid from the absorber to keep the top sheet 30 in a dry state. The interlayer sheet 40 may not be provided.

The material for the interlayer sheet 40 may be the same material as that for the top sheet 30, a spun-laced, spun-bonded, SMS, or pulp non-woven fabric sheet, a sheet of mixture of pulp and rayon, point-bonded paper, or crepe paper, for example. In particular, the air-through non-woven fabric is preferred for its bulkiness. Core-sheath composite fibers are preferably used for the air-through non-woven fabric. The resin for use in the core may be polypropylene (PP) but is preferably polyester (PET) for its high rigidity. The basis weight is preferably 10 to 80 g/m$^2$, more preferably 15 to 65 g/m$^2$. The thickness of the raw fibers in the non-woven fabric is preferably 2.2 to 10 dtex. To make the non-woven fabric high in bulkiness, eccentric fibers with no core in the center, hollow fibers, or eccentric and hollow fibers are preferably used for some or all of the raw fibers.

In the illustrated mode, the interlayer sheet 40 is shorter than the width of an absorber 56 and arranged in the center of the absorber 56. Alternatively, the interlayer sheet 40 may be provided over the entire width of the absorber 56. The longitudinal length of the interlayer sheet 40 may be the same as the length of the absorber 56 or may fall within a shorter-length range centered on the area for receiving the liquid.

(Liquid Impervious Sheet)

There is no particular limitation on the material for the liquid impervious sheet 11. For example, the liquid impervious sheet 11 may be formed from a plastic film made of an olefin resin such as polyethylene or polypropylene, a laminate non-woven fabric sheet in which a plastic film is provided on the surface of non-woven fabric, or a laminate sheet in which non-woven fabric or the like is laid on and joined to a plastic film. The liquid impervious sheet 11 is preferably formed from a liquid impervious and moisture-pervious material having been used preferably in recent years from the viewpoint of stuffiness prevention. As the moisture-pervious plastic film, there has been widely used a microporous plastic film that is obtained by melting and kneading an inorganic filling agent in an olefin resin such as polyethylene or polypropylene to form a sheet and then elongating the sheet in a uniaxial or biaxial direction. Besides, the liquid impervious sheet 11 may be a non-woven fabric sheet of microdenier fibers, or may be a liquid impervious sheet that is formed, without the use of a plastic film, by enhancing leak-preventive performance by reducing the size of air gaps between fibers with the application of heat or pressure or by coating the sheet with a high-water absorption resin, a hydrophobic resin, or a water repellent agent.

The liquid impervious sheet 11 may have a width falling within the back side of the absorbent element 50 as illustrated in the drawing. Alternatively, for enhancement of leak-preventive performance, the liquid impervious sheet 11 may be extended through the both sides of the absorbent element 50 to the both sides of the absorbent element 50 on the top sheet 30 side. The appropriate width of the extended portion is about 5 to 20 mm on each of the right and left sides.

An excretion indicator changed in color by absorption of a liquid may be provided on the inside of the liquid impervious sheet 11, in particular, on the side surfaces of the absorber 56.

(Three-Dimensional Gathers)

The three-dimensional gathers 60 are belt-like members extended entirely along the both sides of the inner body 200 in the front-back direction. The three-dimensional gathers 60 are provided to shut off urine or loose stool moving laterally over the top sheet 30 to prevent lateral leakage of the liquid. In this embodiment, the three-dimensional gathers 60 stand on the sides of the inner body 200. The three-dimensional gathers 60 stand obliquely toward the width-direction central portion at the base-side portions, and stand obliquely toward the width-direction outside at the middle to tip portions.

More specifically, each of the three-dimensional gathers 60 is formed such that a belt-like gather sheet 62 having the same length as the front-back length of the inner body 200 is folded back in two in the width direction, and a plurality of elongated resilient and elastic members 63 is fixed in the extended state along the longitudinal direction at width-direction intervals between the sheets at the folded part and its neighborhood. The base portion of the three-dimensional gather 60 opposite to the tip portion (the end portion opposite to the sheet folded part in the width direction) constitutes an attachment part 65 fixed to the back surface of the inner body 200 at the side edge. The portion of the three-dimensional gather 60 other than the attachment part 65 constitutes a protrusion part 66 (folded-side part) that protrudes from the attachment part 65. The protrusion part 66 is composed of a base-side portion that extends toward the width-direction central side and a tip-side portion that is folded outward in the width direction from the tip of the base-side portion. The three-dimensional gathers in this mode are surface-contact three-dimensional gathers. Alternatively, the three-dimensional gathers may be line-contact three-dimensional gathers that are not folded outward in the width direction (not illustrated). The both front-back end portions of the protrusion parts 66 are front-back fixed portions 67 that are fixed in the fallen state to the side surfaces of the top sheet 30 by a hot-melt adhesive (instead of or in addition to this, a fixing means for material welding such as a heat seal or an ultrasound seal can be used), and front-back intermediate portions of the protrusion parts 66 are non-fixed free portions 68 that are positioned between the front-back fixed portions 67. The elongated resilient members 63 are fixed to the free portions 68 in the front-back direction in the extended state.

The gather sheets 62 may be preferably formed by applying a water repellent treatment with silicon or the like as necessary to flexible non-woven fabric excellent in uniformity and concealing performance such as spun-bonded non-woven fabric (SS, SSS, or the like), SMS non-woven fabric (SMS, SSMMS, or the like), or melt-blown non-woven fabric. The basis weight of the fibers is preferably about 10 to 30 g/m². The elongated resilient and elastic members 63 may be rubber threads or the like. In the case of using spandex rubber threads, the thickness of the threads is preferably 470 to 1240 dtex, more specifically 620 to 940 dtex. The extension ratio of the threads at the time of fixing is preferably 150 to 350%, more specifically 200 to 300%. The "extension ratio" herein takes on a value relative to the natural length as 100%. In addition, a water-proof film 64 may intervene in the gather sheet folded in two as illustrated in the drawing.

The number of the elongated resilient and elastic members 63 provided on the free portions of the three-dimensional gathers 60 is preferably two to six, more specifically three to five. An arrangement interval 60d is appropriately 3 to 10 mm. According to this configuration, the diaper is likely to touch the skin by surface with the elongated resilient and elastic members 63. The elongated resilient and elastic members 63 may be arranged not only at the tip-side portions but also at the base-side portions.

The attachment parts 65 of the three-dimensional gathers 60 may be fixed to an appropriate member such as the top sheet 30, the liquid impervious sheet 11, or the absorbent element 50 in the inner body 200.

In the thus configured three-dimensional gathers 60, the contraction force of the elongated resilient and elastic members 63 acts to make the both front-back end portions closer to each other. The protrusion parts 66 are fixed such the both front-back end portions do not stand, whereas the intermediate portions between the protrusion parts 66 are non-fixed free portions. Accordingly, only the free portions stand to touch the wearer's body as illustrated in FIG. 3. In particular, when the attachment parts 65 are positioned on the back surface of the inner body 200, the three-dimensional gathers 60 stand and open outward in the width direction at the crotch portion and its neighborhood. Accordingly, the three-dimensional gathers 60 are brought into surface contact with the circumferences of the legs to produce an improved fit.

Figure 7:
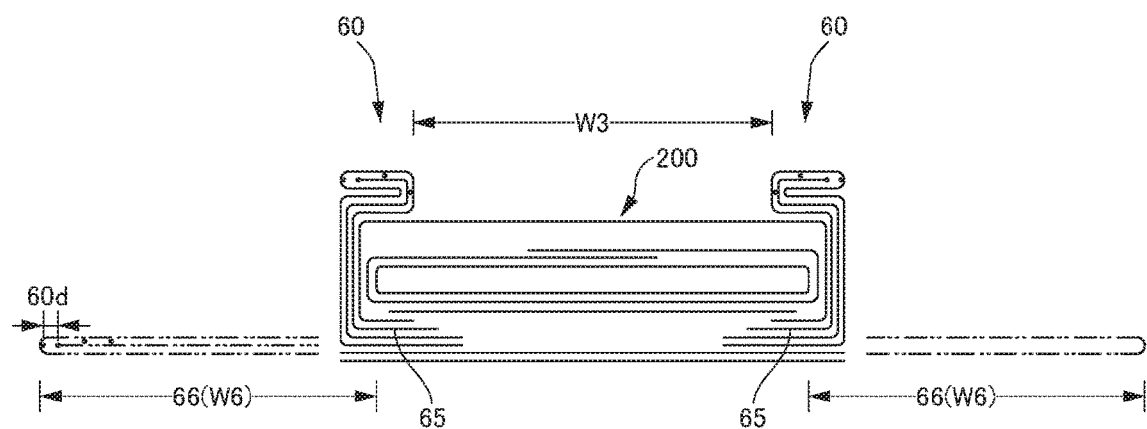
FIG. 7 is a cross-sectional view of main parts of the pants-type disposable diaper.

The dimensions of the three-dimensional gathers 60 can be decided as appropriate. In the case of a disposable diaper for infants, a standing height (width of the protrusion parts 66 in the open state) W6 of the three-dimensional gathers 60 is preferably 15 to 60 mm, more preferably 20 to 40 mm as illustrated in FIG. 7, for example. In addition, when the three-dimensional gathers 60 are flatly folded in parallel to the surface of the top sheet 30, a separation distance W3 between folds on the innermost side is preferably 60 to 190 mm, more preferably 70 to 140 mm.

Unlike in the illustrated example, the three-dimensional gathers may be provided doubly (in two rows) on each of the right and left sides of the inner body 200.

(Absorbent Element)

The absorbent element 50 has the absorber 56 and a wrapping sheet 58 for wrapping the entire absorber 56. The wrapping sheet 58 may not be provided.

(Absorber)

The absorber 56 can be formed from a fiber assembly. The fiber assembly may be accumulated short fibers such as fluff pulp or synthetic fibers or a filament assembly obtained by opening tows (fiber bundles) of synthetic fibers such as cellulose acetate as necessary. The basis weight of the fluffy pulp or accumulated short fibers may be about 100 to 300 g/m², and the basis weight of the filament assembly may be about 30 to 120 g/m², for example. The fineness of synthetic fibers is 1 to 16 dtex, preferably 1 to 10 dtex, more preferably 1 to 5 dtex, for example. In the case of the filament assembly, the filaments may be non-crimped fibers but are preferably crimped fibers. The number of crimps in the crimped fibers may be about 5 to 75 per inch, preferably 10 to 50 per inch, more preferably about 15 to 50 per inch, for example. The crimped fibers are evenly crimped in many cases. High-absorbent polymer particles are preferably dispersed and held in the absorber 56.

Figure 6:
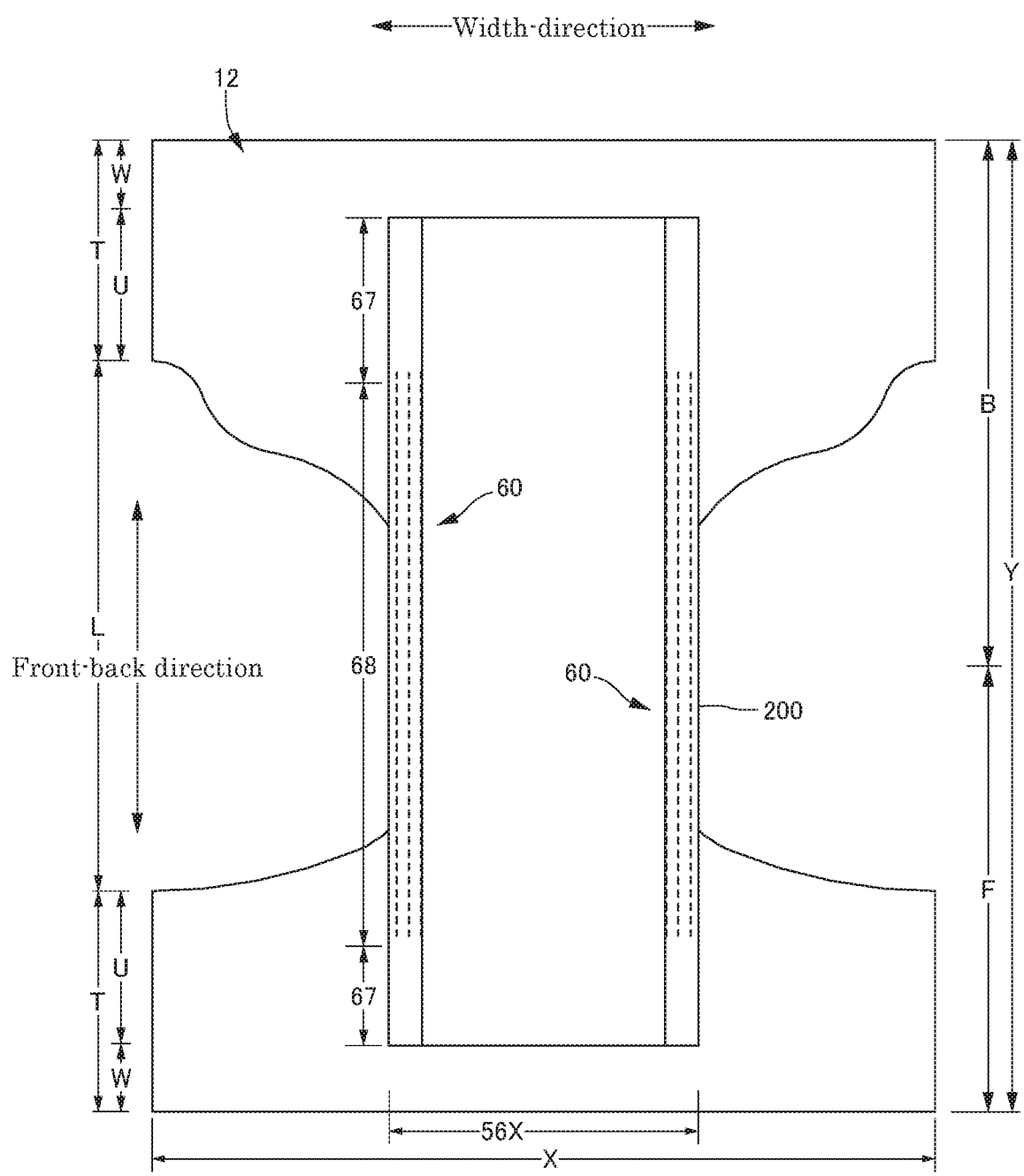
FIG. 6 is a plane view of main parts of the pants-type disposable diaper in the unfolded state.

The absorber 56 may be rectangular in shape but preferably has an hourglass shape with a front end portion, a back end portion, and a narrower portion that is positioned between the front and back end portions and is narrower than the two end portions as illustrated in FIG. 6 to improve the fit of the absorber 56 and the three-dimensional gathers 60 to the circumferences of the legs.

The dimensions of the absorber can be decided as appropriate. Nevertheless, the absorber preferably extends to the peripheral edges or their neighborhoods of the inner body in the front-back direction and the width direction. Reference sign 56X represents the width of the absorber 56.

(High-Absorbent Polymer Particles)

The absorber 56 may partially or entirely contain high-absorbent polymer particles. The high-absorbent polymer particles include "powder" as well as "particles". The high-absorbent polymer particles 54 may be particles to be generally used in this type of absorbent article. For example, when being screened by the use of a standard 500-μm screen (JIS Z8801-1: 2006) (5-minute shaking), the ratio of the particles left on the screen is desirably 30 weight % or less, and when being screened by the use of a standard 180-μm screen (JIS Z8801-1: 2006) (5-minute shaking), the ratio of the particles left on the screen is desirably 60 weight % or more.

There is no particular limitation on the material for the high-absorbent polymer particles but the material preferably has a water absorption capacity of 40 g/g or more. The high-absorbent polymer particles may be based on starch, cellulose, or synthetic polymer. The high-absorbent polymer particles may be made of a starch-acrylate graft copolymer, a saponified substance of starch-acrylonitrile copolymer, a crosslinking substance of carboxymethyl-cellulose sodium, an acrylate polymer, or the like. The high-absorbent polymer particles are preferably used in a general particulate form but may be used in another form.

The water absorption rate of the high-absorbent polymer particles is preferably 70 seconds or less, in particular 40 seconds or less. At too low a water absorption rate, the absorbed liquid is more likely to flow back from the absorber 56 to the outside.

The basis weight of the high-absorbent polymer particles can be decided as appropriate according to the absorbing capability required for the use of the absorber 56. Although not definitely specified, the basis weight may be 50 to 350 $g/m^2$. When the basis weight of the polymer is less than 50 $g/m^2$, it is difficult to provide the necessary absorbing capability. When the basis weight of the polymer exceeds 350 $g/m^2$, the absorbing effect becomes saturated.

If necessary, the high-absorbent polymer particles can be adjusted in dispersing density or dispersing quantity along the planar direction of the absorber 56. For example, the dispersing quantity of the high-absorbent polymer particles may be larger in the excretion area than the other areas. With regard to gender differences, the dispersing density (quantity) of the high-absorbent polymer particles may be increased at the front side of the product for male, and may be increased at the central portion of the product for female. In addition, the polymer may not be provided locally (in spots, for example) in the planar direction of the absorber 56.

(Wrapping Sheet)

The material for the wrapping sheet 58 may be tissue paper, in particular, crepe paper, non-woven fabric, polyethylene-laminated non-woven fabric, a porous sheet, or the like. However, the material sheet is desirably configured to retain the high-absorbent polymer particles. In the case of using non-woven fabric instead of crepe paper, the hydrophilic SMS non-woven fabric (SMS, SSMMS, or the like) is preferred in particular and its material may be polypropylene, polyethylene/polypropylene composite, or the like. The basis weight of the material is desirably 5 to 40 $g/m^2$, in particular 10 to 30 $g/m^2$.

The form of wrapping by the wrapping sheet 58 can be decided as appropriate. Nevertheless, from the viewpoint of ease of manufacture and prevention of leakage of the high-absorbent polymer particles from the front and back end edges, the wrapping sheet 58 preferably wraps the absorber 56 in a cylindrical form to surround the front and back surfaces and both side surfaces of the absorber 56, and has front and back end portions extended off from the front and back sides of the absorber 56 so that the extended portions are crushed on the top and bottom sides and joined together by a joining means such as a hot-melt adhesive.

(Outer Body)

Figure 8:
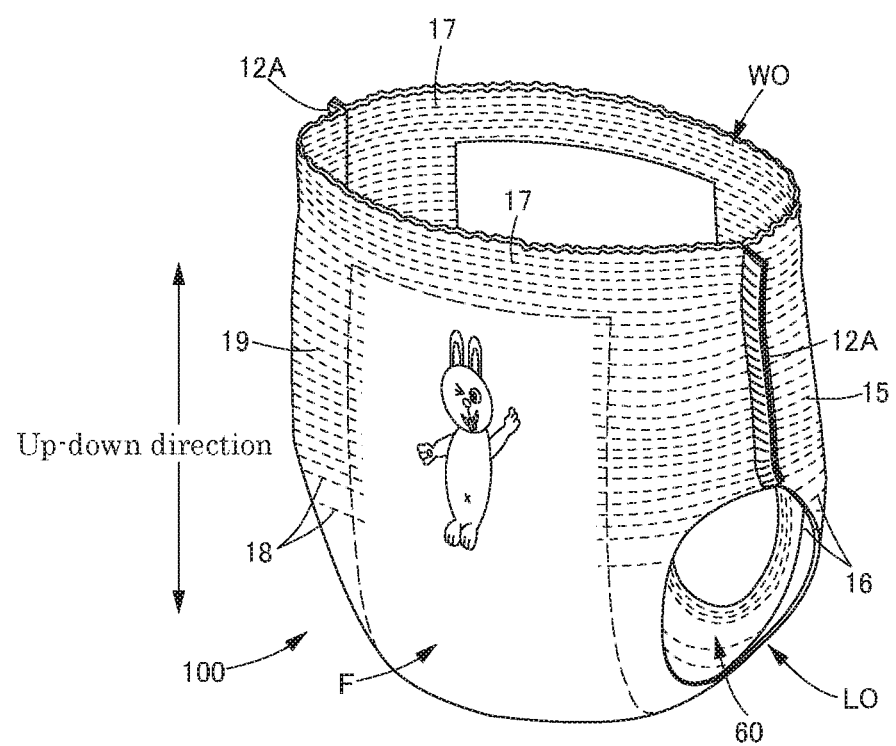
FIG. 8 is a perspective view of the pants-type disposable diaper.

The outer body 12 has a part constituting a front body part F extended from the front-back center to the ventral side and a part constituting a back body part B extended from the front-back center to the back side. The front body part F and the back body part B are joined together at the both sides to form side seal portions 12A, thereby forming a waist opening WO through which the wearer's waist is passed and a pair of right and left leg openings LO through which the wearer's legs are passed as illustrated in FIG. 8.

The outer body 12 has a waist portion T determined as a vertical range having side seal portions 12A (vertical range from the waist opening WO to the upper ends of the leg openings LO), and an intermediate portion L determined as a front-back range forming the leg openings LO (between the vertical area having the side seal portions 12A of the front body part F and the vertical area having the side seal portions 12A of the back body part B). The waist portion T is conceptually divided into a "waist edge portion" W forming the edge of the waist opening and a "lower waist portion" U as a portion under the waist edge portion W. In general, when there are boundaries in the waist portion T with changes in width-direction expansion and contraction stress (for example, changes in the thickness or extension ratio of the resilient and elastic members), the part nearer the waist opening WO than the boundary nearest the waist opening WO constitutes the waist edge portion W. When there are no boundaries, the part nearer the waist opening WO than the absorber 56 or the inner body 200 constitutes the waist edge portion W. The lengths of these parts vary depending on the size of the product and can be decided as appropriate. As an example, the length of the waist edge portion W may be 15 to 40 mm, and the length of the lower waist portion U may be 65 to 120 mm. The both ends of the intermediate portion L are narrowed along the circumferences of the wearer's legs, and the wearer's legs are placed through the narrowed ends. As a result, the outer body 12 has an almost hourglass shape as a whole. The degree of narrowing of the outer body 12 can be decided as appropriate. As in the mode illustrated in FIGS. 1 to 8, the outer body 12 is preferably narrower than the inner body 200 at the narrowest area for simple appearance. Alternatively, the outer body 12 may be wider than the inner body 200 even at the narrowest area.

The outer body 12 is formed by bonding two sheet materials 12S and 12H by an adhesive such as a hot-melt adhesive as illustrated in FIGS. 3 to 5. The inner sheet material 12H positioned inside extends up to the edge of the waist opening WO, whereas the outer sheet material 12S wraps around the edge of the inner sheet material 12H on the waist side and folds back toward the inside. Folded parts 12r are extended to cover the upper end portion of the inner body 200 on the waist side.

There is no particular limitation on the sheet materials 12S and 12H as far as they are sheet material, but they are preferably formed from non-woven fabric. There is no specific limitation on raw fibers for the non-woven fabric. For example, the raw fibers may be synthetic fibers based on olefin such as polyethylene or polypropylene, polyester, or polyamide, reproduced fibers of rayon, cupra, or the like, natural fibers of cotton or the like, or mixed fibers or composite fibers of two or more of the foregoing fibers. The non-woven fabric may be produced by any processing method. The processing method may be any of publicly known methods such as spun-lacing, spun-bonding, thermal bonding, melt-blowing, needle-punching, air-through processing, and point-bonding, for example. In the case of using non-woven fabric, its basis weight is preferably about 10 to 30 g/m$^2$.

The total basis weight of the outer body 12 is preferably about 20 to 60 g/m$^2$ to allow the designs of printed sheets 25 described later to be favorably seen through the outer body 12 from the outer surface of the product. The total light transmittance of the outer body 12 defined by JIS K 7105 is preferably 40% or more, in particular 50% or more.

The outer body 12 has elongated resilient and elastic members 15 to 19 such as rubber threads provided at a predetermined extension ratio between the sheet materials 12S and 12H to enhance the fit to the wearer's waist. The elongated resilient and elastic members 15 to 19 may be formed from synthetic rubber or natural rubber. The two sheet materials 12S and 12H in the outer body 12 can be bonded to each other and the elongated resilient and elastic members 15 to 19 can be sandwiched and fixed between the sheet materials 12S and 12H by the means of hot-melt adhesion in various application patterns, heat sealing, or ultrasound adhesion. Fixing firmly the entire outer body 12 is not preferred because this deteriorates the hand feeling of the sheet. Taking this into account, it is preferred that the elongated resilient and elastic members 15 to 19 are firmly bonded and the other parts are not bonded or are lightly bonded.

More specifically, in the waist edge portions W of the back body part B and the front body part F, a plurality of waist edge portion resilient and elastic members 17 is fixed in an extended state along the width direction at a predetermined extension ratio with up-down intervals in such a manner as to be entirely continuous in the width direction, between the inner surface of the inner sheet material 12H and the outer surfaces of the folded parts 12r of the outer sheet material 12S. One or more of the waist edge portion resilient and elastic members 17 in the area adjacent to the lower waist portion U may overlap the inner body 200 or may be provided on the both sides of the central portion in the width direction with the exception of the central portion in the width direction overlapping the inner body 200. As the waist edge portion resilient and elastic members 17, about 3 to 22 rubber threads with a thickness of about 155 to 1880 dtex, in particular about 470 to 1240 dtex (this is applied to a synthetic rubber, and in the case of a natural rubber, a cross-section area of about 0.05 to 1.5 mm$^2$, in particular about 0.1 to 1.0 mm$^2$) are preferably fixed at an extension ratio of about 150 to 400%, in particular about 220 to 320%, and at intervals of 4 to 12 mm. All of the waist edge portion resilient and elastic members 17 may not be equal in thickness and extension ratio. For example, the resilient and elastic members may be different in thickness and extension ratio between the upper and lower sides of the waist edge portion W.

In the lower waist portions U of the front body part F and the back body part B, a plurality of lower waist portion resilient and elastic members 15 and 19 composed of elongated resilient and elastic members is fixed in an extended state along the width direction at a predetermined extension ratio with up-down intervals in such a manner as to be entirely continuous in the width direction, between the outer surface of the inner sheet material 12H and the inner surface of the outer sheet material 12S on the upper side and both sides of the central portion in the width direction with the exception of the central portion in the width direction overlapping the inner body 200.

As the lower waist portion resilient and elastic members 15 and 19, about 5 to 30 rubber threads with a thickness of 155 to 1880 dtex, in particular about 470 to 1240 dtex (this is applied to a synthetic rubber, and in the case of a natural rubber, a cross-section area of about 0.05 to 1.5 mm$^2$, in particular about 0.1 to 1.0 mm$^2$) are preferably fixed at an extension ratio of about 200 to 350%, in particular about 240 to 300%, and at intervals of 1 to 15 mm, in particular 3 to 8 mm.

In the intermediate portions L of the front body part F and the back body part B, a plurality of intermediate portion resilient and elastic members 16 composed of elongated resilient and elastic members is fixed in an extended state along the width direction at a predetermined extension ratio with up-down intervals in such a manner as to be entirely continuous in the width direction between the outer surface of the inner sheet material 12H and the inner surface of the outer sheet material 12S on the both sides of the central portion in the width direction with the exception of the central portion in the width direction overlapping the inner body 200.

As the intermediate portion resilient and elastic members 16 and 18, about 2 to 10 rubber threads with a thickness of about 155 to 1880 dtex, in particular about 470 to 1240 dtex (this is applied to a synthetic rubber, and in the case of a natural rubber, a cross-section area of 0.05 to 1.5 mm$^2$, in particular about 0.1 to 1.0 mm$^2$) are preferably fixed at an extension ratio of 150 to 300%, in particular 180 to 260%, and at intervals of 5 to 40 mm, in particular 5 to 20 mm.

When the lower waist portion resilient and elastic members and the intermediate portion resilient and elastic members 15, 19, 16, and 18 are provided on the both sides of the central portion in the width direction with the exception of the central portion in the width direction overlapping the inner body 200 as illustrated in the drawings, the inner body 200 does not contract more than necessary in the width direction, does not become fluffy with deterioration in appearance, or does not decrease in absorbing performance. The foregoing mode includes the mode in which the resilient and elastic members reside only on the width-direction both sides, and the mode in which the resilient and elastic members reside crossing over the inner body 200 from one to the other sides in the width direction, but the resilient and elastic members are finely cut and exert no contraction force on the width-direction central portion overlapping the inner body 200 (this substantially means that no resilient and elastic members are provided), and thus the contraction force of the resilient and elastic members acts only on the width-direction both sides. As a matter of course, the arrangement modes of the lower waist portion resilient and elastic members and the intermediate portion resilient and elastic members 15, 19, 16, and 18 are not limited to the foregoing ones. Alternatively, some or all of the lower waist portion resilient and elastic members and the intermediate portion resilient and elastic members 15, 19, 16, and 18 may be provided crossing over the inner body 200 from the one to the other sides in the width direction so that the contraction force acts on the entire lower waist portions U in the width direction.

In the case in which the elongated resilient and elastic members 15 to 19 of the respective parts cross over the printed sheets 25 described later, the elongated resilient and elastic members 15 to 19 preferably have a low content of titanium oxide (for example, 2% or less) when a rubber containing titanium oxide is used or do not preferably contain titanium oxide at all.

(Printed Sheets)

The printed sheets 25 with printed designs are provided between the liquid impervious sheet 11 and the outer body 12 (including the layers in the outer body 12). The outer body 12 may not be provided to expose the printed sheets 25 on the outer surface. The printed sheets 25 in the illustrated example are smaller in area than the body parts on which they are arranged, and are individually provided on the front body part F and the back body part B. Alternatively, the printed sheet 25 may be continuously provided from the front body part F through the crotch portion to the back body part B.

There are no particular limitations on the dimensions and shape of the printed sheets 25. However, it is preferred that the printed sheets 25 are sufficiently large in area to be fully functional. For example, the width of the printed sheets 25 is preferably about 50 to 120% of the width of the absorber 56, and the length of the printed sheets 25 is preferably about 15 to 30% of the article entire length Y on at least one of the ventral side and the back side. The shape of the printed sheets 25 is preferably rectangular as in the illustrated example in terms of eliminating trim loss, but the printed sheets 25 may be cut in any other geometric shape such as circle, oval, triangle, or hexagon, or in any shape along the periphery of the design.

The sheet material for the printed sheets 25 may be a plastic film, non-woven fabric, paper, or the like, but is preferably a bulky and highly air-permeable material. In the case of using the plastic film, it is desirably moisture permeable due to prevention of stuffiness. The non-woven fabric and paper are preferred for their moisture permeability. To provide some printed designs, the non-woven fabric is preferably high in smoothness for easy printing, and the paper is preferably high in strength to make ink blurring less prone to occur. Preferred in particular are crepe paper (tissue paper) with a basis weight of about 15 to 35 $g/m^2$ and a thickness of about 0.1 to 0.3 mm, and non-woven fabric with a basis weight of about 10 to 25 $g/m^2$ and a thickness of about 0.1 to 0.3 mm (specifically, spun-bonded non-woven fabric or SMS non-woven fabric with a fineness of about 1.0 to 3.0 dtex at a spun-bonded portion). In the case of using the crepe paper, it preferably has a crepe ratio of about 5 to 20%, in particular about 5 to 15%. The crepe paper with a crepe ratio of 20% or more is not suitable for design printing because a larger amount of ink is fixed but blurred. The crepe paper with a crepe ratio of 5% or less has an insufficient ink penetration, thereby resulting in a smaller amount of ink fixation.

(Outer Body Separation Structure)

In the foregoing example, the integral outer body 12 covers continuously from the front body part F to the back body part B. Alternatively, the outer body may be divided into a ventral-side outer body covering the ventral side of the wearer's waist and a back-side outer body covering the back side of the same such that the front end portion of the inner body is coupled by a hot-melt adhesive or the like to the inner surface of the width-direction central portion of the ventral-side outer body and the back end portion of the inner body is coupled by a hot-melt adhesive or the like to the inner surface of the width-direction central portion of the back-side outer body, and the ventral-side outer body and the back-side outer body are not continued but separated on the crotch side. The separation distance may be about 150 to 250 mm. In this case, a crotch portion outer body may be fixed to the back surface of the liquid impervious sheet of the inner body to cover the entire back surface of the inner body or the entire exposed portion between the ventral-side outer body and the back-side outer body. As the crotch portion outer body, the same material can be used as the foregoing one for the outer body. The crotch portion outer body is also equivalent to the outer body of the present invention.

(Anti-odor Tape)

Figure 9:
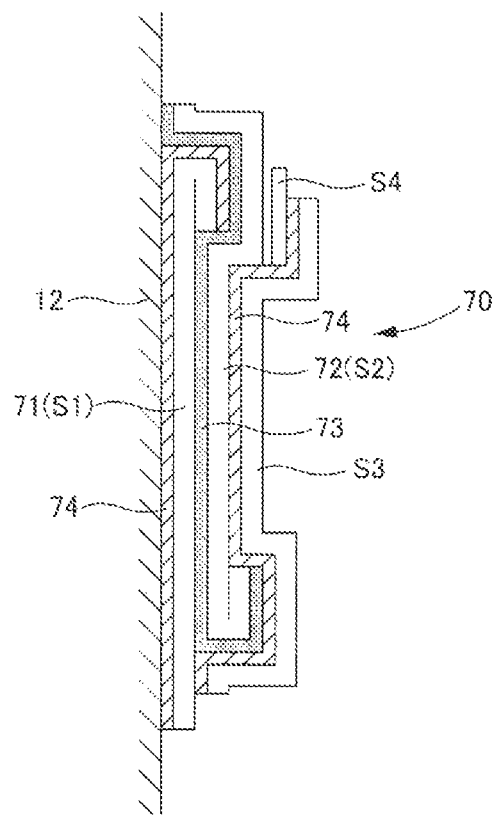
FIG. 9 is a side view of an anti-odor tape.
Figure 10:
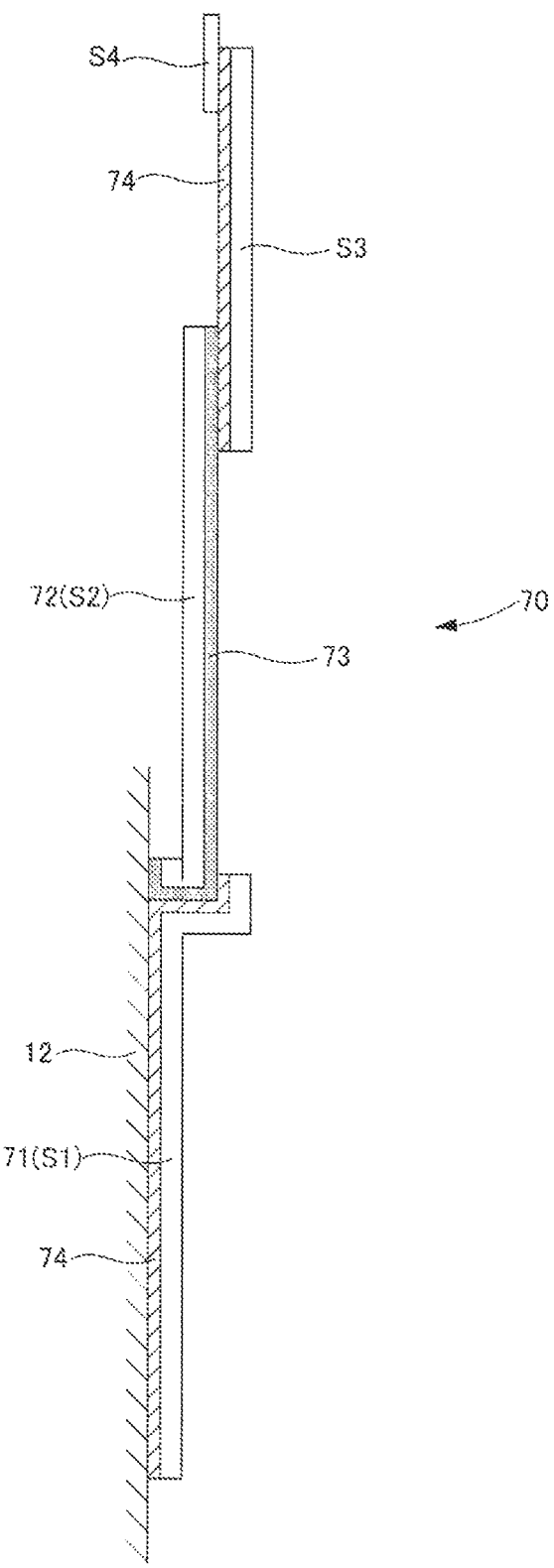
FIG. 10 is a side view of the anti-odor tape.

An anti-odor tape 70 (also serving as a post-processing tape as described later) is provided on the outer surface of the back body part B of the outer body 12 in the width-direction central portion. Specifically, the anti-odor tape 70 includes a first gas barrier layer 71 coupled to the outer surface of the outer body 12 and a second gas barrier layer 72 stuck in a separable manner to the outer surface of the first gas barrier layer 71 via an adhesive agent 73 containing an anti-odor agent as illustrated in FIG. 9. At the time of disposal of the diaper, the second gas barrier layer 72 is separated from the first gas barrier layer 71 to expose the adhesive agent 73 to the outside, thereby taking an anti-odor measure as illustrated in FIG. 10.

As described above, the anti-odor tape 70 is structured such that the adhesive agent 73 containing the anti-odor agent is sandwiched between the first gas barrier layer 71 and the second gas barrier layer 72 to enclose the anti-odor agent in the first gas barrier layer 71, the second gas barrier layer 72, and the adhesive agent 73, and the anti-odor agent takes effect by the user's separating operation, and this structure makes performance degradation less prone to occur. In addition, the adhesive agent 73 obtaining the anti-odor agent is exposed to the outside at the time of disposal of the diaper, and the anti-odor agent is not hidden inside at the time of disposal and its anti-odor effect is not suppressed. Accordingly, the anti-odor tape 70 is excellent in anti-odor effect at the time of disposal. In addition, the anti-odor agent hardly takes effect during use of the absorbent article, and therefore there is no fear that it is difficult to recognize the time for replacement of the diaper by the odor of the excretion.

The adhesive agent 73 containing the anti-odor agent may be configured such that a separation treatment such as a peeling agent is applied to the surface of either one of the gas barrier layers, so that, when the second gas barrier layer 72 is separated from the first gas barrier layer 71, the adhesive agent 73 is left only on the surface of the other gas barrier layer (in the illustrated example, the second gas barrier layer) as in the illustrated example, or the adhesive agent 73 containing the anti-odor agent may be configured such that the adhesive agent 73 is left on both the first gas barrier layer 71 and the second gas barrier layer 72 (that is, the second gas barrier layer 72 is removed in the thickness-direction center of the adhesive agent 73 layer). In the former mode, when the second gas barrier layer 72 is removed, the adhesive agent 73 layer is left on the first gas barrier layer 71 residing on the diaper.

In the illustrated mode, the first gas barrier layer 71 is fixed directly to the outer surface of the diaper. Alternatively, the first gas barrier layer 71 may be coupled indirectly to the outer surface of the diaper via another member (the term "coupling" in the present invention includes direct fixing and coupling and also indirect coupling). Meanwhile, the second gas barrier layer 72 may be coupled to the first gas barrier layer 71, may be completely separable from the first gas barrier layer 71, or may be partially fixed in a separable manner to the outer surface of the diaper. The second gas barrier layer 72 may include a fixing means for fixing directly or indirectly to the outer surface of the diaper after separation from the first gas barrier layer 71 to prevent the situation in which the second gas barrier layer 72 is attached again to the first gas barrier layer 71. In addition, in the mode in which, after the separation, the adhesive agent 73 containing the anti-odor agent is left on both the first gas barrier layer 71 and the second gas barrier layer 72, the exposed area of the adhesive agent 73 can be doubled in the presence of the fixing means. In the illustrated example, the fixing means is composed of an adhesive agent 74 on a third sheet S3 described later. Alternatively, the fixing means may be another one such as a hook material for a mechanical fastener.

There is no specific limitation on the first gas barrier layer 71 and the second gas barrier layer 72 as far as they have gas barrier properties. As an example, they are preferably sheets of synthetic resin including olefin-based resin such as polyethylene or polypropylene, polyvinyl chloride, or PET. Each of the first gas barrier layer 71 and the second gas barrier layer 72 may be composed of a single layer or plural layers. The degree of gas barrier properties of the gas barrier layers 71 and 72 can be decided as appropriate. Their oxygen permeability measured in conformity with JIS K 7126 is preferably 10,000 cc/(m²·24 Hr·atm) or less, more preferably 5,000 cc/(m²·24 Hr·atm) or less. The gas barrier layers 71 and 72 may be the same or different in gas barrier properties. For example, when the first gas barrier layer 71 and the second gas barrier layer 72 are different in gas barrier properties, the gas barrier properties of the second gas barrier layer 72 positioned more outside than the first gas barrier layer 71 are preferably higher. When a gas barrier layer is further provided outside the first gas barrier layer 71 and the second gas barrier layer 72 as in the illustrated mode, the gas barrier properties of the gas barrier layers closer to the adhesive agent 73 containing the anti-odor agent are preferably higher (that is, in the illustrated mode, the gas barrier properties of the first gas barrier layer 71 and the second gas barrier layer 72 are higher than those of the outside gas barrier layer).

There is no particular limitation on the adhesive agent 73, and the adhesive agent 73 may be a synthetic rubber-based adhesive agent, a natural rubber-based adhesive agent, an acrylic resin-based adhesive agent, a silicon resin-based adhesive agent, or the like.

The anti-odor agent mixed in the adhesive agent 73 can be at least one of a perfume and an odor-adsorption agent. The perfume may be a natural aromatic or a synthetic aromatic but is preferably the one prepared to have the effect of masking the odor of the excretion (the effect of competing or countervailing against the odor to make the odor less felt), in particular, the harmonization effect (the effect of harmonizing with the odor to make the odor felt as not discomfort). Specific examples of perfumes are natural extracted aromatic materials such as ambergris, benzoin, castor, civet, clove oil, galbanum, jasmine absolute, labdanum, mate, melilot, mimosa, tonkin musk, myrrh, oakmoss, frankincense, Angelica dahurica, orris, patchouli, rosemary oil, santal oil, vetiver oil, and violet leaf absolute; various synthetic aromatic materials such as higher alcohol, aldehyde, benzaldehyde, benzoic acid, cinnamic acid, cinnamic aldehyde, cinnamic alcohol, coumarin, ester, indole, ketone, salicylic acid and its related compounds, terpenoid, and vanillin; or mixtures of two or more of the foregoing ones, but are not limited to them. Other commercially available aromatic materials can be also widely used. The aromatics are preferably high in volatility. In the case of using an aromatic material, about 1 to 5 weight % of aromatic material is preferably contained in the adhesive agent 73. At the time of disposal, the area of the outside exposed surface of the adhesive agent 73 is preferably about 500 to 3000 mm². When the content of aromatic material is too small, it is unfavorably required to increase the outside exposed area of the adhesive agent 73. When the content of aromatic material is too large, it may unfavorably lead to a reduction in the adhesive force of the adhesive agent 73. In addition, when the area of the outside exposed surface of the adhesive agent 73 is too small, it is necessary to increase the content of aromatic material, thereby leading to a reduction in the adhesive force. When the area of the outside exposed surface of the adhesive agent 73 is too large, it may make it difficult to assure the adhesive force.

The odor-adsorption agent may be a deodorant agent (physical adsorption) or an odor-eliminating agent (chemical adsorption), or may be a combination of the two. The odor-adsorption agent may be a solid such as particles or a liquid. The deodorant agent may be one or more of publicly known deodorant agents such as activated carbon, silica gel, zeolite (aluminosilicate of a three-dimensional skeletal structure), layered-structure particles composed of zirconium phosphate, three dimensional-structure particles composed of silicate, or zinc oxide. In addition, the odor-eliminating agent may be one or more of publicly known ones without particular limitation. The odor-eliminating agent may be the one containing metallic ions chemically adsorbing odor molecules, for example, the one formed by substituting some or all of exchangeable ions in a substance with silver ions, copper ions, zinc ions, or the like. More specifically, for example, the odor-eliminating agent may be the particles formed by substituting some or all of the exchangeable ions in zeolite with silver ions (Zeomic (registered trademark) produced by Sinanen Zeomic Co., Ltd. is commercially available), the particles formed by substituting some or all of the exchangeable ions in zirconium phosphate with copper ions ($Zr_3(PO_4.Cu^{2+})$), the particles formed by substituting some or all of the exchangeable ions in silicate with copper ions, zinc oxide particles, the particles formed by substituting some or all of the exchangeable ions in silicate with zinc ions, or the like. As an example, an odor-eliminating (chemical adsorption) reaction equation by the copper ions is as shown below. In this case, the odor molecules and the metallic ions are coordinately bonded to form complex ions.

$$Cu^{2+}+H_2S \rightarrow H_2S:Cu^{2+}$$

The anti-odor agent may be sealed in micro capsules as described in Patent Document 1. However, the adhesive 73 containing the anti-odor agent of the present invention is not used as a fixing means for fastener tapes unlike in Patent Document 1 (the adhesive agent as a fixing means for fastener tapes is bonded to the outer surface of the diaper at the time of disposal and is not exposed to the outside), which hardly causes a reduction in adhesive force. In addition, the anti-odor agent is enclosed in the first gas barrier layer 71, the second gas barrier layer 72, and the adhesive agent 73 and is less prone to cause performance degradation. Therefore, it is preferred that the anti-odor agent is not sealed in micro capsules but is directly mixed for a simpler structure.

Figure 11:
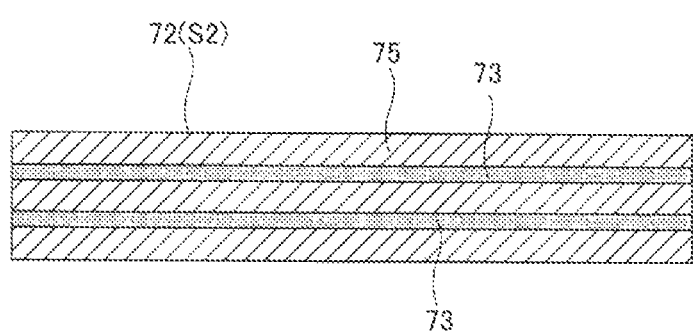
FIG. 11 is a plane view of main parts of the anti-odor tape.

The adhesive agent 73 for bonding the first gas barrier layer 71 and the second gas barrier layer 72 may all be the adhesive agent 73 containing the anti-odor agent. However, although the anti-odor agent is enclosed in the first gas barrier layer 71, the second gas barrier layer 72, and the adhesive agent 73, the peripheral surface of the adhesive agent 73 is exposed to the outside between the first gas barrier layer 71 and the second gas barrier layer 72. Accordingly, performance degradation progresses in the anti-odor agent due to the exposed part, although it is a limited amount, even before the separation of the second gas barrier layer 72. Therefore, it is preferred to apply the adhesive agent 73 containing the anti-odor agent in an elongated pattern and block the longitudinal both side edges of the adhesive agent by extending an adhesive agent 75 not containing the anti-odor agent as illustrated in FIG. 11. In this case, the both sides of the adhesive agent 73 containing the anti-odor agent in the direction orthogonal to the longitudinal side thereof (equal to the longitudinal side of the anti-odor tape 70 in the illustrated mode) may be blocked by the adhesive agent 75 not containing the anti-odor agent as in the illustrated mode. Alternatively, the entire circumference of the adhesive agent 73 containing the anti-odor agent may be surrounded by the adhesive agent 75 not containing the anti-odor agent. In addition, as in the mode illustrated in FIG. 11, the adhesive agent 73 containing the anti-odor agent may be provided in a plurality of places at intervals along the front surfaces of the first gas barrier layer 71 and the second gas barrier layer 72.

Figure 17:
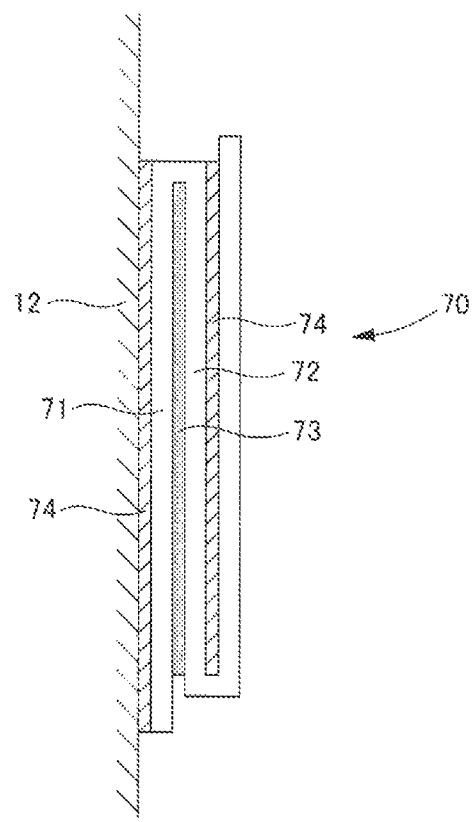
FIG. 17 is a side view of the anti-odor tape.
Figure 18:
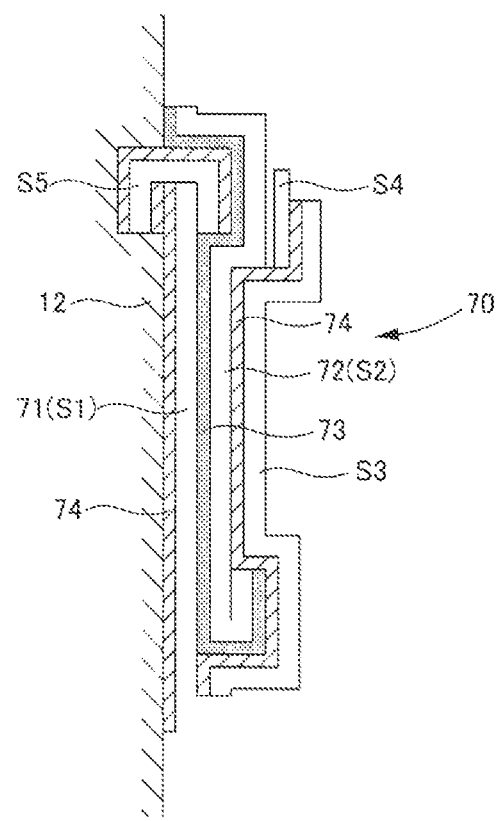
FIG. 18 is a side view of the anti-odor tape.

The first gas barrier layer 71 and the second gas barrier layer 72 of the anti-odor tape 70 may be completely separate members. However, as illustrated in FIG. 9, the first gas barrier layer 71 and the second gas barrier layer 72 are desirably composed of a pair of adjacent layers in which a belt-like body with gas barrier properties (the gas barrier material described above can be used) is folded plural times in the longitudinal direction and the adjacent layers are bonded via the adhesive agent 73 to form a folded structure. In this case, the belt-like body may be formed by coupling a plurality of sheets S1 to S4 as in the mode illustrated in FIG. 9 or may be formed from a single sheet as illustrated in FIG. 17. In the case of coupling a plurality of sheets to form the belt-like body, there is no particular limitation on the number of the sheets. The belt-like sheet may be composed of four sheets as illustrated in FIG. 9 or may be composed of five sheets S1 to S5 as illustrated in FIG. 18, or may be composed of a smaller or larger number of sheets.

In the mode in which the belt-like body is folded plural times as described above, all the adhesive agents 73 and 74 may not necessarily contain the anti-odor agent but at least the adhesive agent 73 to be bonded to at least part of the surface of the belt-like body to be on the outside at the time of disposal needs to contain the anti-odor agent. From the viewpoint of adhesive force, the adhesive agent 74 not to be exposed to the outside at the time of disposal desirably does not contain the anti-odor agent, but may contain the anti-odor agent.

The mode illustrated in FIG. 9 will be further described in detail. The anti-odor tape 70 also serves as a post-processing tape used to fix the absorbent article in the rolled state. The anti-odor tape 70 is structured such that the belt-like bodies S1 to S4 with gas barrier properties are folded plural times in the longitudinal direction into a state in which a plurality of layers is stacked and the adjacent layers are bonded via the adhesive agents 73 and 74. When the anti-odor tape 70 is unfolded, either one of the front and back surfaces is the surface with the adhesive agent 74 for fixing the diaper in the rolled state, and part of the other surface is the surface with the adhesive agent 73 containing the anti-odor agent. The anti-odor tape 70 is preferably formed by the post-processing tape as described above because the anti-odor measure can be automatically taken at the time of disposal. In addition, in this mode, the adhesive agent 74 for post-processing fixation and the adhesive agent 73 containing the anti-odor agent are separate members. Since the adhesive agent 74 for post-processing fixation does not contain the anti-odor agent, it is possible to prevent reduction in fixing force (as a matter of course, the adhesive agent 74 for post-processing fixation may contain the anti-odor agent).

Figure 16:
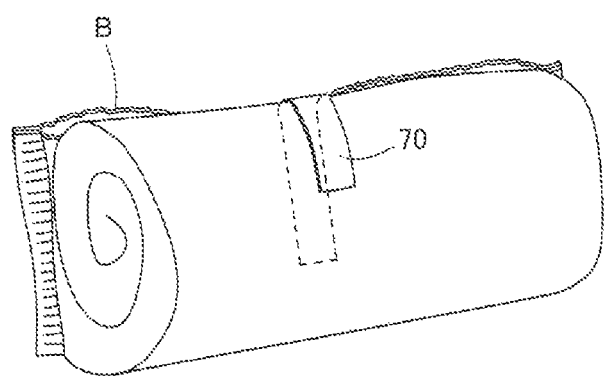
FIG. 16 is a perspective view of the pants-type disposable diaper in a post-processed state.

In the post-processing and anti-odor tape 70 in the illustrated mode, the adhesive agent 73 is applied to the surface on the outer body 12 side, the first sheet S1 fixed by the adhesive agent 73 to the outer surface of the outer body 12, the second sheet S2 coupled to the outwardly folded tip portion of the first sheet S1, and the third sheet S3 fixed to the outwardly folded tip portion of the second sheet S2 form a three-fold (Z-shaped in cross section) structure, and the second sheet S2 is bonded in a separable manner to the first sheet S1 by the adhesive agent 73 applied to the surface on the first sheet S1 side, and the third sheet S3 is bonded in a separable manner to the second sheet S2 by the adhesive agent 74 applied to the surface on the second sheet S2. The sheets S1 to S3 are made separable from one another by applying a separation treatment such as a peeling agent to the surfaces opposite to the adhesive agent 73. The parts of the sheets S1 to S3 where the adhesive agents 73 and 74 are bonded together and the parts of the sheets S1 to S3 to be adhered to the outer body 12 are coupled together in an inseparable manner. The colored tape S4 in an opaque color such as white is coupled by the adhesive agent 74 to the tip portion of the third sheet S3 to form a visible tab part. At the time of disposal, the diaper 100 is rolled or folded such that the top sheet 30 is positioned inside and the front body part F is positioned inside, then the post-processing and anti-odor tape 70 is separated and extended, and wound around the rolled or folded diaper 100 from the back body part B through the waist opening WO to the outer surface on the opposite side, and then is fixed by the adhesive agent 74 on the third sheet S3 as illustrated in FIG. 16. At that time, the adhesive agent 73 on the second sheet S2 is exposed to the outside. Accordingly, in the post-processing and anti-odor tape 70 of Z-fold structure, at least the adhesive agent 73 on the second sheet S2 contains the anti-odor agent, and the first sheet S1 and the second sheet S2 are set as the first gas barrier layer 71 and the second gas barrier layer 72 of the present invention, whereby the adhesive agent 73 can be exposed to the outside at the time of disposal. In this case, the adhesive agents 74 on the first sheet S1 and the third sheet S3 desirably do not contain the anti-odor agent but may contain the same.

The post-processing and anti-odor tape 70 as described above preferably has a width of 10 mm or more and a length of 50 mm or more, taking into account the fact that the tab part is picked up and the diaper is rolled and fastened.

Figure 12A:
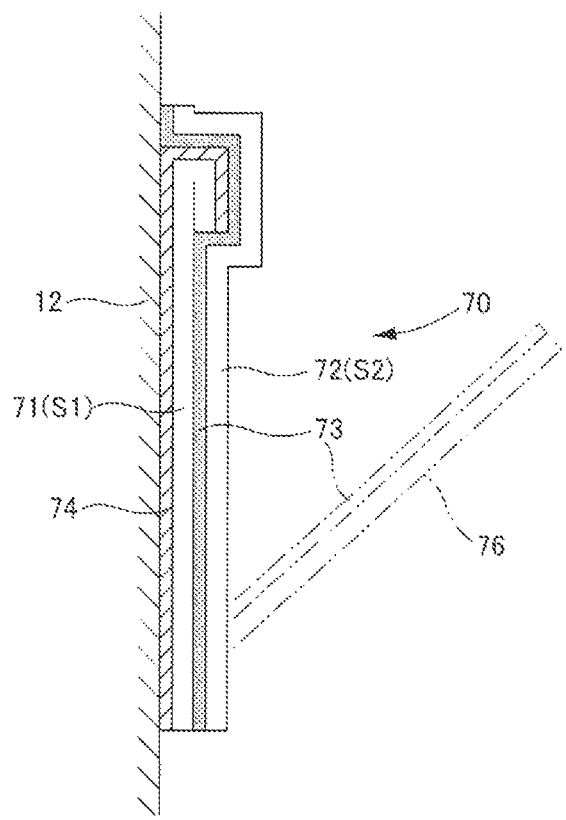
FIG. 12(a) is a side view of the anti-odor tape and FIG. 12(b) is a plane view of the same.
Figure 12B:
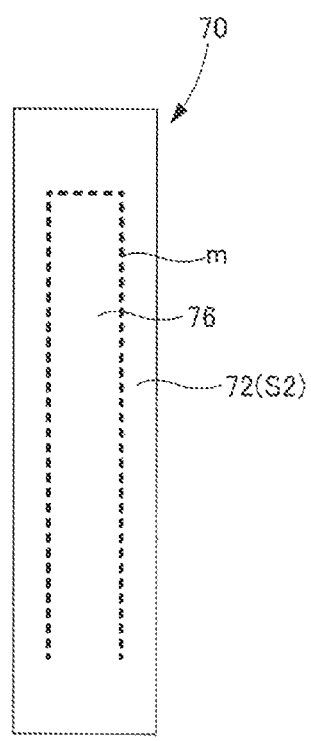
Figure 13:
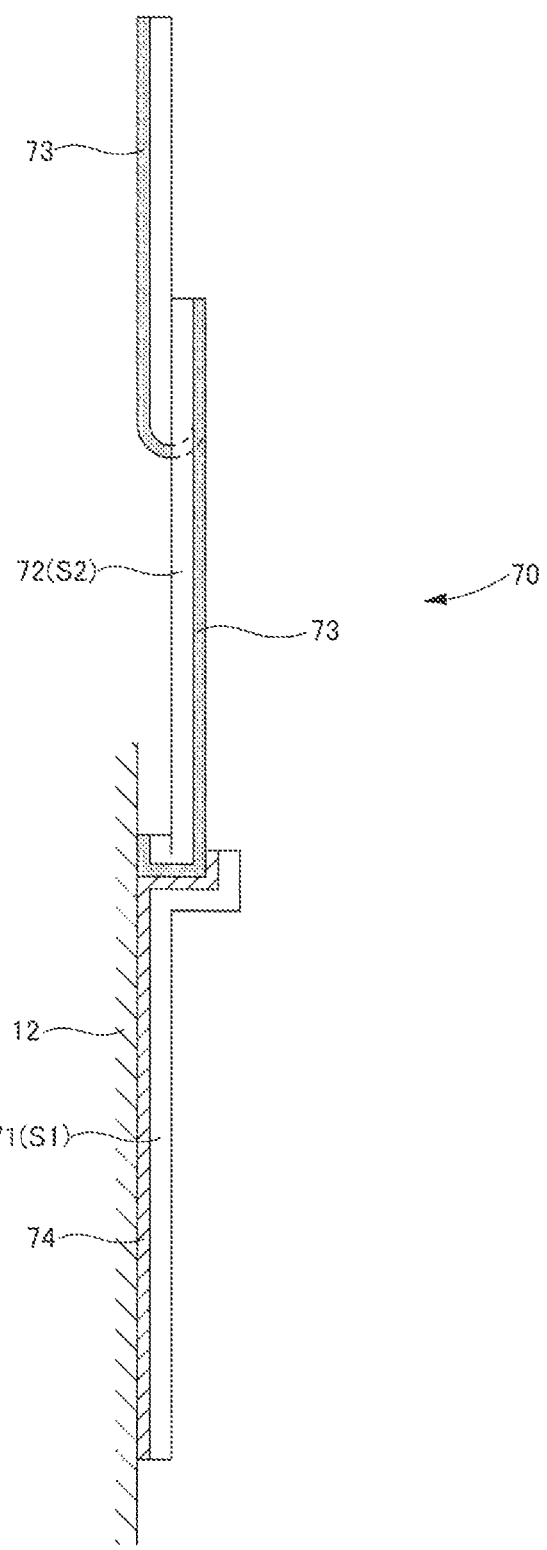
FIG. 13 is a side view of the anti-odor tape.

Any other publicly-known post-processing tape may be applied as far as it is structured such that the adhesive agent containing the anti-odor agent is exposed to the outside at the time of disposal. FIGS. 12 and 13 illustrate a mode that is basically the same as the mode illustrated in FIG. 9 except that a part 76 of the second sheet S2 is surrounded by U-shaped perforations m (or may be cut in advance) so that the part 76 can be cut and raised, and that the third sheet S3 and its adhesive agent 74, and the fourth sheet S4 are eliminated. In this case, the adhesive agent 73 on the cut-and-raised part 76 of the second sheet S2 is used to fix the diaper in the post-processing and the adhesive agent 73 on the other part of the second sheet S2 is exposed to the outside. JP-A No. H11-76302 describes a similar post-processing tape with which the present invention can be carried out by containing the anti-odor agent in the adhesive agent.

Figure 19:
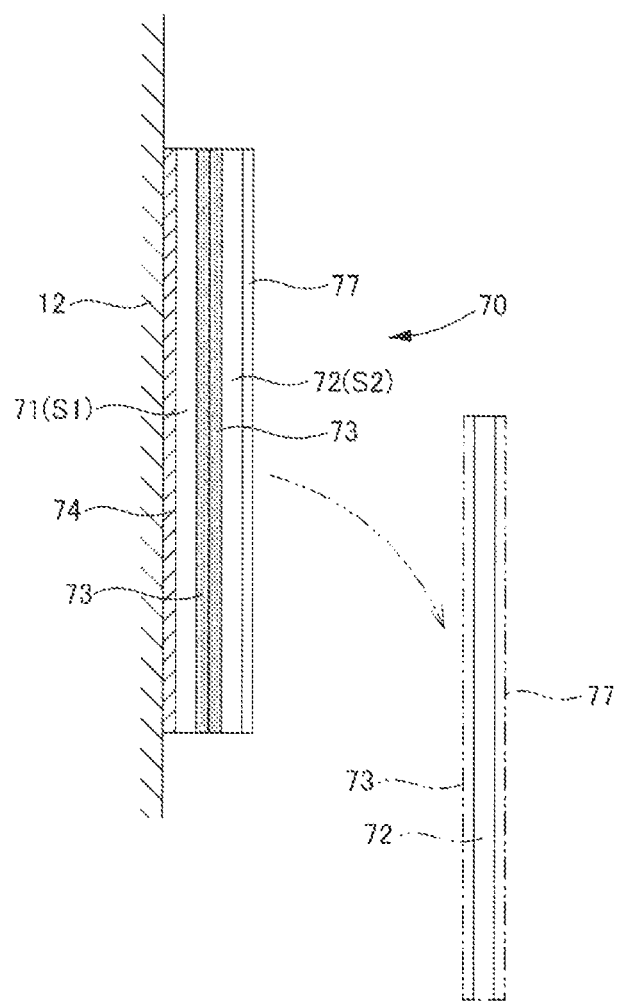
FIG. 19 is a side view of the anti-odor tape.

Alternatively, as illustrated in FIG. 19, the post-processing tape may be configured such that the first sheet S1 constituting the first gas barrier layer 71 is fixed to the outer surface of the diaper, the second sheet S2 constituting the second gas barrier layer 72 is bonded by the adhesive agent 73 in a separable manner to the first sheet S1, and the adhesive agent 73 is left on both the first sheet S1 and the second sheet S2 when the second sheet S2 is separated from the first sheet S1. In this mode, the anti-odor measure is taken by separating completely the second sheet S2 from the first sheet S1 to use the second sheet S2 as a single post-processing tape and exposing the adhesive agent 73 left on the surface of the first gas barrier layer 71 to the outside. JP-A No. H07-250865 describes a similarly-structured post-processing tape with which the present invention can be carried out by containing the anti-odor agent in the adhesive agent.

Figure 14:
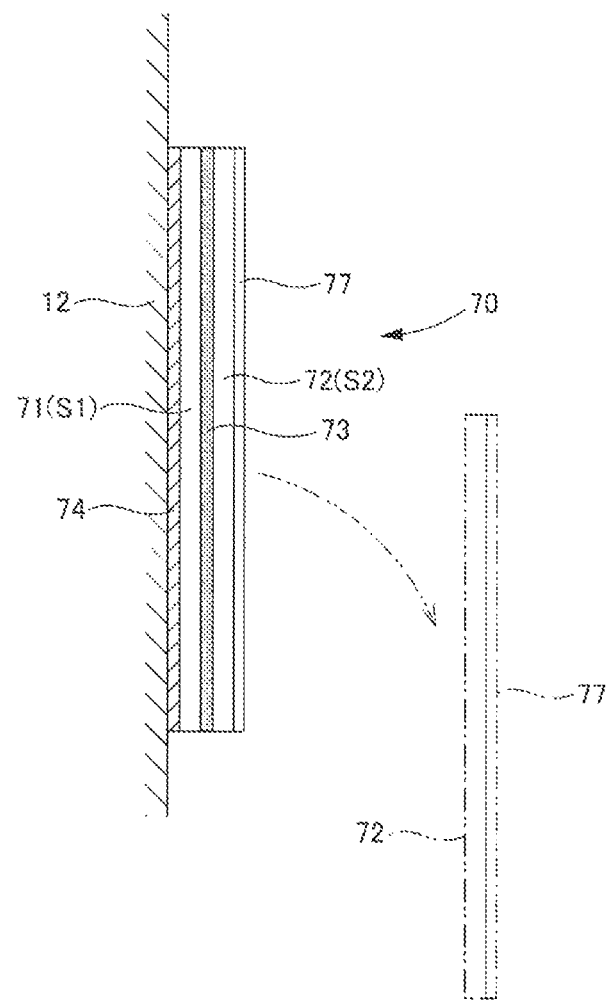
FIG. 14 is a side view of the anti-odor tape.
Figure 15:
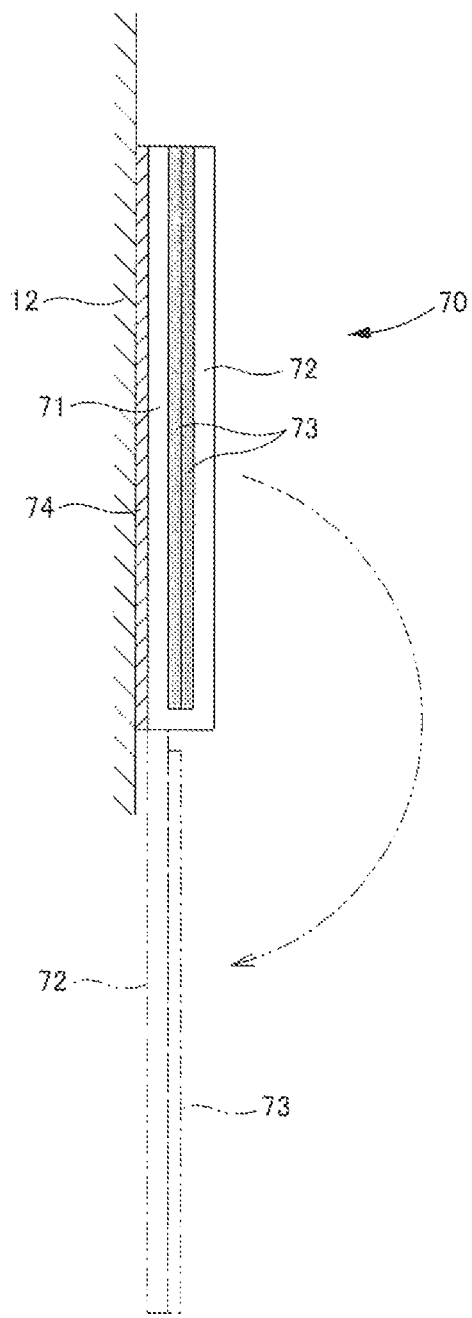
FIG. 15 is a side view of the anti-odor tape.

Meanwhile, the anti-odor tape 70 may not serve as a post-processing tape but may be dedicated for anti-odor measure and provided in an appropriate place such as the outer surface of the diaper. In this case, the anti-odor tape 70 may have the foregoing structure or may be configured as illustrated in FIG. 14 such that the first sheet S1 constituting the first gas barrier layer 71 is fixed to the outer surface of the diaper, the second sheet S2 constituting the second gas barrier layer 72 is bonded by the adhesive agent 73 in a separable manner to the first sheet S1, and the second gas barrier layer 72 is separated and removed to expose the adhesive agent 73 left on the surface of the first gas barrier layer 71 to the outside. In this mode, the exposed area of the adhesive agent 73 and the shape and arrangement of the anti-odor tape 70 can be freely designed to take a more desired anti-odor measure. Alternatively, the anti-odor tape 70 may be configured as illustrated in FIG. 15 such that the belt-like body having gas barrier properties is folded in two to form the first gas barrier layer 71 and the second gas barrier layer 72, and the opposed surfaces of the first gas barrier layer 71 and the second gas barrier layer 72 are bonded to each other by the adhesive agent 73 containing the anti-odor agent. In these modes, a print 77 of characters or patterns can be applied to the outer surface of the second gas barrier layer 72. In this example, the adhesive agent 73 is also left on the surface of the second gas barrier layer 72 and is exposed to the outside. Alternatively, the adhesive agent 73 may not be left on the second gas barrier layer 72.

The anti-odor tape 70 can be provided in an appropriate place of the absorbent article as far as the adhesive agent is exposed to the outside (not hidden) at the time of disposal. When the anti-odor tape 70 also serves as a post-processing tape for the pants-type disposable diaper as in the mode of FIG. 9, the anti-odor tape 70 is generally provided on the back body part B. Alternatively, the anti-odor tape 70 may be provided on the front body part F or may be provided on both the back body part B and the front body part F.

<Others>

The present invention is also applicable to a fastener tape in the tape-type disposable diaper. In the fastener tape as described in Patent Document 1, even if the adhesive agent on the target tape contains the anti-odor agent, the adhesive agent is not exposed to the outside at the time of disposal. Accordingly, the fastener tape is preferably configured to have a part that is to be exposed to the outside at the time of disposal and is sandwiched between the first gas barrier layer and the second gas barrier layer in the product state, and the adhesive agent containing the anti-odor agent is provided on the part sandwiched between the first gas barrier layer and the second gas barrier layer.

When a perfume is used as the anti-odor agent mixed into the adhesive agent 73, the perfume can be contained in the part of or entire absorber 56. The perfume contained in the absorber 56 preferably emits a less strong fragrance at the initial stage of the use in both the case in which the perfume is emitted immediately after the manufacture and the case in which the fragrance starts to take effect on contact with the moisture of an excretion such as urine as a trigger. This is because the strong fragrance may cause the user a discomfort feeling or may make it difficult to recognize the time for replacement of the diaper by the odor of the excretion. However, the weak fragrance may not produce a sufficient anti-odor effect after excretion. That is, the strength of the fragrance as an anti-odor measure in the absorbent article needs to become higher gradually for a sufficient anti-odor effect from the stage of start of use to the stage of disposal. In contrast, in the case of using the perfume as the anti-odor agent mixed in the adhesive agent 73, containing the perfume also in the part of or entire absorber 56 makes it possible to increase the strength of the fragrance in stages before and after the separation of the anti-odor tape 70, whereby the anti-odor measure with the perfume in the absorbent article can be more preferred. For example, in the case where the release of the perfume is started immediately after the manufacture, the strength of the perfume is modest at the start of use, and then the anti-odor tape 70 is separated at an arbitrary subsequent stage, for example after the excretion or at the time of disposal, to make the strength of the fragrance (anti-odor effect) higher. In addition, in the case where the perfume takes effect on contact with the moisture of an excretion such as urine as a trigger, the fragrance is non-existent or suppressed at the start of use, then the fragrance is emitted at the time of excretion to a degree that an anti-odor measure can be taken against the odor of the excretion, and then the anti-odor tape 70 is separated at an arbitrary subsequent stage, for example at the time of disposal, to make the strength of the fragrance (anti-odor effect) higher. In addition, using both the perfume to emit a fragrance immediately after the manufacture and the perfume to take effect on contact with an excretion as a trigger makes it possible to make the fragrance stronger in three stages.

The perfume added to the absorber 56 preferably has the same fragrance as that of the perfume contained in the adhesive agent 73, but may have a different fragrance. In any case, the entire amount of perfume to be diffused increases after the separation of the anti-odor tape 70 to allow the user to feel the fragrance becoming stronger. The "addition" of the perfume includes both meanings of external addition and internal addition (addition to a raw material). In addition, the "perfumes having the same fragrance" include both the perfumes of the same ingredients and the perfumes that are different in ingredients but have the same fragrance. The perfumes that are different in ingredients but have the same fragrance mean the perfumes felt to have the same fragrance by humans. More specific examples are the perfumes with the same name of fragrance (for example, the perfumes called the ones with the fragrance of lemon are regarded as the perfumes with the same fragrance even though they are different in ingredients), and the perfumes that are merely different in volatility or are different in ingredients such as solvents other than the fragrance ingredient, and the like. Further, regardless of the differences in ingredient and name, the "perfumes having the same fragrance" include the perfumes that are determined as having the same fragrance by the fragrance evaluation test described below.

(Fragrance Evaluation Test)

Samples: Prepared by applying two kinds of perfumes to filter paper with a width of 15 mm and a basis weight of 125 g/m² such that the additive amount per area was equal to that in the anti-odor tape.

Examinees: 40 or more women at ages of 20 to 40 (the examinees' ages are preferably dispersed in an even manner).

Test method: The examinees checked the fragrance of the first sample for ten seconds, and after an interval of 30 seconds, they checked the fragrance of the second sample. The examinees compared the fragrance of the first sample and the fragrance of the second sample, and made answers on the comparison result by one of five choices "The two are completely the same," "The two are almost the same," "Not sure," "The two are slightly different," and "The two are completely different."

Judgment: The two were determined as "the same" if the examinees with the answer "The two are completely the same" and the examinees with the answer "The two are almost the same" accounted for 80% or more of all the examinees.

In the case of causing the perfume contained in the absorber 56 to take effect on contact with moisture of an excretion such as urine as a trigger, the perfume can be the one that emits a fragrance by the aromatic ingredient's reaction with the moisture, the one that is included in an inclusion substance, or the like. Among them, the perfume is preferably included in an inclusion substance because it is possible to prevent a fragrance loss due to volatility, suppress the emission of the fragrance before use, and increase the strength of the fragrance during and after use. The inclusion substance can be one or more selected from cyclodextrin, xanthan gum, guar gum, and pectin. In particular, cyclodextrin is preferred because it not only emits a fragrance but also adsorbs effectively an odorous component of the excretion. The perfume emitting a fragrance by the aromatic ingredient's reaction with moisture may be a water-soluble perfume (essence) that is formed by solving an aroma base in alcohol and water and then extracted for use in drinks or the like.

In the case of adding the perfume to the absorber 56, it is preferred to prepare a perfume-contained solution by mixing the perfume into water or the like and spray the same onto the absorber 56 by a spray device or the like. At that time, an antiseptic agent may be added to the perfume-contained solution to prevent the propagation of bacteria in the perfume-contained solution in a tank and the generation of mold in the produced absorber 56 due to an increased amount of moisture. The perfume-contained solution can be composed of 86.9 weight % of water, 10.3 weight % of α-cyclodextrin, 1 weight % of perfume, and 1.8 weight % of antiseptic agent, for example. The perfume-contained solution may be sprayed onto the absorber by about 0.4 to 0.8 g per 10 g of the absorber.

The perfume-contained solution may be added to the absorber 56 at the same time as the mixture of the fiber assembly and the high-absorbent polymer particles. Alternatively, the perfume-contained solution may be sprayed onto the formed absorber 56, or when the fiber assembly is formed of cotton-like pulp by crushing and accumulating a pulp sheet, the perfume-contained solution may be contained in the pulp sheet before the crushing by application or the like.

Further, it goes without saying that instead of or in addition to the addition of the perfume to the absorber 56, the perfume may be added to materials other than the absorber 56 such as non-woven fabric, films, resilient members, wrapping sheets, printed sheets, and the like to produce the same advantage as that in the case of adding the perfume to the absorber 56.

By reducing the strength of the odor emitted from the absorbent article, the effect of the anti-odor agent of the present invention becomes more significant. Accordingly, it is preferred to use highly antibacterial and odor-eliminating high-absorbent polymer particles, add an antimicrobial agent to the absorber 56 so as not to generate odors due to the decomposition of an excretion by bacteria, and use highly antibacterial and odor-eliminating materials for the other components.

<Effect Verification Test>

As described in Table 1, pants-type disposable diapers different in the presence or absence of a perfume and the use mode of the perfume were manufactured and subjected to sensory evaluation of the strength of a fragrance in different situations.

Example 1 was a sample of the same structure as illustrated in FIGS. 1 to 10. The post-processing tape was wide as described in Table 1 and the perfume was added to the adhesive agent on the post-processing tape.

Comparative example 1 was the same as Example 1 except that the width of the post-processing tape was standard and the perfume was not contained in the adhesive agent on the post-processing tape but was evenly sprayed onto the entire surface of the absorber, whereby the usage of the perfume was increased. The same perfume was used in Example 1 and Comparative example 1.

Comparative example 2 was the same as the comparative example 1 except that the perfume was not used.

For each of the examples, a before-use sample (one week after manufacture), an after-use sample (one week after manufacture), and an after-use sample (one month after manufacture) were prepared. Thirty examinees checked the fragrances of the samples at a temperature of 25° C. and a relative humidity of 50%. They evaluated the strengths of the fragrances on a scale of five levels (0, 0.5, 1.0, 1.5, and 2.0) with the strength of the fragrance of the comparative example 1 before use as 1.0. The averages of the evaluation values were set as evaluation results.

Before-use samples (one week after manufacture): Sealed in vinyl packages and stored for one week after manufacture at a temperature of 25° C. and a relative humidity of 50%. One of the samples was taken out of the package and put into a plastic bag, and then was checked for a fragrance five minutes later.

After-use samples (one week after manufacture): Sealed in vinyl packages and stored for one week after manufacture at a temperature of 25° C. and a relative humidity of 50%. The absorbers in the samples were caused to absorb 150-cc ion-exchange water. Then, the samples were rolled and fastened by the post-processing tapes, and put into plastic bags and checked for fragrances five minute later.

After-use samples (one month after manufacture): Sealed in vinyl packages and stored for one month after manufacture at a temperature of 25° C. and a relative humidity of 50%. The absorbers in the samples were caused to absorb 150-cc ion-exchange water. Then, the samples were rolled and fastened by the post-processing tapes, and put into plastic bags and checked for fragrances five minute later.

The terms "before-use" and "after-use" in this test are based on the before-use and after-use states of the pants-type disposable diaper. As in the foregoing description, the "before-use" means the unused state without absorption of ion-exchange water, and the "after-use" means the state in which the sample absorbing ion-exchange water instead of urine is rolled and fastened with the post-processing tape.

Table 1 shows the test results. The example 1 according to the present invention has been found to suppress the fragrance before use and feel sufficiently the fragrance after use as compared to the comparative example 1 in which the perfume was sprayed onto the absorber.

TABLE 1

|  | Example 1 | Comparative Example 1 | Comparative Example 2 |
|---|---|---|---|
| Structure of post-processing tape | Four Z-fold structure members (the same as illustrated in FIG. 9) | Four Z-fold structure members (the same as illustrated in FIG. 9) | Four Z-fold structure members (the same as illustrated in FIG. 9) |
| Dimensions of post-processing tape (unused state) | 39 mm wide × 58 mm long | 13 mm wide × 58 mm long | 13 mm wide × 58 mm long |
| Use of perfume | Presence | Presence | Absence |
| Where to add perfume | Mixed into adhesive agent on post-processing tape (adhesive agent (73) in FIG. 9) | Sprayed onto absorber 56 | — |
| Used amount of perfume per diaper (g) | 0.0017 | 0.0035 | — |
| Content of adhesive agent (g/m²) | 15 | — | — |
| Ratio of added perfume to adhesive agent (weight %) | 5 | — | — |
| Strength of fragrance (before-use/one week after manufacture) | 0.1 | 1.0 | 0.0 |
| Strength of fragrance (after-use/one week after manufacture) | 1.8 | 1.8 | 0.0 |
| Strength of fragrance (after-use/one month after manufacture) | 1.8 | 1.6 | 0.0 |

<Descriptions of the Terms Used Herein>

Unless otherwise specified herein, the terms used herein have the meanings described below.

The "front-back (vertical) direction" refers to the direction linking the ventral side (front side) and the back side (rear side), and the "width direction" refers to the direction (right-left direction) orthogonal to the front-back direction.

The "extension ratio" refers to a value with respect to 100% representing the natural length.

The "basis weight" is measured in such a manner as described below. That is, a sample or a test piece is preliminarily dried and left stand in a test room or a test device in a standard state (at a temperature of 20±5° C. and a relative humidity of 65% or less) until reaching a constant weight. The preliminary drying refers to turning the sample or the test piece to a constant weight in an environment at a relative humidity of 10 to 25% and a temperature not exceeding 50° C. The preliminary drying is not necessary for fibers with an official moisture regain of 0.0%. The test piece of the constant weight is cut into a 200 mm×250 mm (±2 mm) sample by the use of a basis weight plate (200 mm×250 mm±2 mm). The weight of the sample is measured and the measured value is multiplied by 20 to determine the weight per square meter as a basis weight.

The "thickness" is automatically measured by an automated thickness gauge (KES-G5 handy compression tester) on the conditions that the load is 10 gf/cm² and the pressure area is 2 cm²).

The water absorption capacity is measured by carrying out JIS K7223-1996 "Testing method for water absorption capacity of super absorbent polymers."

The water absorption rate is determined as "time that elapses before the end point" by carrying out JIS K7224-1996 "Testing method for water absorption rate of super absorbent polymers" using 2 g of high absorbent polymer and 50 g of saline.

When there are no descriptions of environmental conditions for tests and measurements, the tests and measurements are performed in a test room or a test device in a standard state (at a temperature of 20±5° C. and a relative humidity of 65% or less).

INDUSTRIAL APPLICABILITY

The present invention is suited for pants-type disposable diapers with post-processing tapes as in the foregoing example. However, the present invention is also usable for all absorbent articles such as tape-type disposable diapers, pad-type disposable diapers, incontinence pads, and sanitary napkins.

REFERENCE SIGNS LIST

11 Liquid impervious sheet
12 Outer body
12A Side seal portion
12r Folded part
25 Printed sheet
200 Inner body
30 Top sheet
40 Interlayer sheet
50 Absorbent element
56 Absorber
58 Wrapping sheet
60 Three-dimensional gather
62 Gather sheet
71 First gas barrier layer
72 Second gas barrier layer
73 Adhesive agent
70 Anti-odor tape
S1 First sheet
S2 Second sheet
S3 Third sheet

The invention claimed is:

1. An absorbent article comprising an anti-odor post-processing tape that has:
   a first gas barrier layer having an inner surface and an outer surface;
   a second gas barrier layer having an inner surface and an outer surface; and
   a third layer having an inner surface and an outer surface, wherein the inner surface of the first gas barrier layer is opposite to an outer surface of the absorbent article, the outer surface of the first gas barrier layer is opposite to the inner surface of the second gas barrier layer, and the outer surface of the second gas barrier layer is opposite to the inner surface of the third layer, wherein the inner surface of the first gas barrier layer is fixed to the outer surface of the absorbent article only via a non-anti-odor adhesive not containing an anti-odor agent, a first portion of the inner surface of the second gas barrier layer is stuck to the outer surface of the first gas barrier layer in a separable manner via an anti-odor adhesive containing an anti-odor agent and a second portion of the inner surface of the second gas barrier layer is fixed to the outer surface of the absorbent article via the anti-odor adhesive, and the inner surface of the third layer is stuck to the outer surface of the second gas barrier layer in a separable manner only via a non-anti-odor adhesive not containing an anti-odor agent, wherein the anti-odor post-processing tape has a three-layered structure formed by folding a belt-like body with gas barrier property longitudinally twice such that the anti-odor post-processing tape has a Z-shape in cross section, the first gas barrier layer is an innermost layer of the three-layered structure, at time of disposal of the absorbent article, the anti-odor post-processing tape folded to have the Z-shape in the cross section is unfolded by separating the third layer together with a whole of the non-anti-odor adhesive from the second gas barrier layer and separating the second gas barrier layer from the first gas barrier layer, the third layer of the unfolded anti-odor post-processing tape has a surface having the non-anti-odor adhesive to be stuck outside to the absorbent article for fixing the absorbent article in a rolled state, and the anti-odor adhesive is thereby exposed to outside to take an anti-odor measure; and wherein the anti-odor adhesive is applied in an elongated shape between the first gas barrier layer and the second gas barrier layer, and a non-anti-odor adhesive is extended along both longitudinal side edges of the anti-odor adhesive.

2. The absorbent article according to claim 1, wherein the anti-odor agent is mixed into the anti-odor adhesive and the anti-odor agent is not in a microcapsules form.

3. The absorbent article according to claim 1, wherein the anti-odor agent includes a perfume, and at least some components of the absorbent article other than the anti-odor post-processing tape also include the perfume.

4. An absorbent article comprising an Multi-odor post-processing tape that has:

a first gas barrier layer having an inner surface and an outer surface;

a second gas barrier layer having an inner surface and an outer surface; and a third layer having an inner surface and an outer surface, wherein the inner surface of the first gas barrier layer is opposite to an outer surface of the absorbent article, the outer surface of the first gas barrier layer is opposite to the inner surface of the second gas barrier layer, and the outer surface of the second gas barrier layer is opposite to the inner surface of the third layer, wherein the inner surface of the first gas barrier layer is fixed to the outer surface of the absorbent article only via a non-anti-odor adhesive not containing an anti-odor agent, a first portion of the inner surface of the second gas barrier layer is stuck to the outer surface of the first gas barrier layer in a separable manner via an anti-odor adhesive containing an anti-odor agent and a second portion of the inner surface of the second gas barrier layer is fixed to the outer surface of the absorbent article via the anti-odor adhesive, and the inner surface of the third layer is stuck to the outer surface of the second gas barrier layer in a separable manner only via a non-anti-odor adhesive not containing an anti-odor agent, wherein the anti-odor post-processing tape has a three-layered structure formed by folding a belt-like body with gas barrier property longitudinally twice such that the anti-odor post-processing tape has a Z-shape in cross section, the first gas barrier layer is an innermost layer of the three-layered structure, the belt-like body with gas barrier property is made by coupling a first sheet forming the first gas barrier layer, a second sheet constituting the second gas barrier layer and a third sheet constituting the third layer in this order, at time of disposal of the absorbent article, the anti-odor post-processing tape folded to have the Z-shape in the cross section is unfolded by separating the third layer together with a whole of the non-anti-odor adhesive from the second gas barrier layer and separating the second gas barrier layer from the first gas barrier layer, the third layer of the unfolded anti-odor post-processing tape has a surface having the non-anti-odor adhesive to be stuck outside to the absorbent article for fixing the absorbent article in a rolled state, and the anti-odor adhesive is thereby exposed to outside to take an anti-odor measure; and wherein the anti-odor adhesive is applied in an elongated shape between the first gas barrier layer and the second gas barrier layer, and a non-anti-odor adhesive is extended along both longitudinal side edges of the anti-odor adhesive.

5. An absorbent article comprising an anti-odor post-processing tape that has:

a first gas barrier layer having an inner surface and an outer surface;

a second gas barrier layer having an inner surface and an outer surface; and a third layer having an inner surface and an outer surface, wherein the inner surface of the first gas barrier layer is opposite to an outer surface of the absorbent article, the outer surface of the first gas barrier layer is opposite to the inner surface of the second gas barrier layer, and the outer surface of the second gas barrier layer is opposite to the inner surface of the third layer, wherein the inner surface of the first gas barrier layer is fixed to the outer surface of the absorbent article only via a non-anti-odor adhesive not containing an anti-odor agent, the inner surface of the second gas barrier layer is stuck to the outer surface of the first gas barrier layer in a separable manner via an anti-odor adhesive containing an anti-odor agent, and the inner surface of the third layer is stuck to the outer surface of the second gas barrier layer in a separable manner only via a non-anti-odor adhesive not containing an anti-odor agent, wherein the anti-odor post-processing tape has a three-layered structure formed by folding a belt-like body with gas barrier property longitudinally twice such that the anti-odor post-processing tape has a Z-shape in cross section, the first gas barrier layer is an innermost layer of the three-layered structure, the belt-like body with gas barrier property is made from a single sheet, at time of disposal of the absorbent article, the anti-odor post-processing tape folded to have the Z-shape in the cross section is unfolded by separating the third layer together with a whole of the non-anti-odor adhesive from the second gas barrier layer and separating the second gas barrier layer from the first gas barrier layer, the third layer of the unfolded anti-odor post-processing tape has a surface having the non-anti-odor adhesive to be stuck outside to the absorbent article for fixing the absorbent article in a rolled state, and the anti-odor adhesive is thereby exposed to outside to take an anti-odor measure; and wherein the anti-odor adhesive is applied in an elongated shape between the first gas barrier layer and the second gas barrier layer, and a non-anti-odor adhesive is extended along both longitudinal side edges of the anti-odor adhesive.

6. The absorbent article according to claim 1, wherein the non-anti-odor adhesive contacts both longitudinal side edges of the anti-odor adhesive.

* * * * *

UNITED STATES PATENT AND TRADEMARK OFFICE
CERTIFICATE OF CORRECTION

PATENT NO. : 11,517,484 B2
APPLICATION NO. : 15/511371
DATED : December 6, 2022
INVENTOR(S) : Takeshi Kurohara, Yosuke Mori and Takashi Hagi It is certified that error appears in the above-identified patent and that said Letters Patent is hereby corrected as shown below:

In the Claims

Column 25, Line 3 of Claim 1:
"second gas harrier layer..."
Should instead read:
--second gas barrier layer...--

Column 25, Line 51 of Claim 4:
"...Multi-odor post-processing tape..."
Should instead read:
--...anti-odor post-processing tape...--

Signed and Sealed this
Seventh Day of February, 2023

Katherine Kelly Vidal
*Director of the United States Patent and Trademark Office*